US010071245B1

United States Patent
Phillips et al.

(10) Patent No.: US 10,071,245 B1
(45) Date of Patent: Sep. 11, 2018

(54) THINKING CAP: COMBINING PERSONALIZED, MODEL-DRIVEN, AND ADAPTIVE HIGH DEFINITION TRANS-CRANIAL STIMULATION (HD-TCS) WITH FUNCTIONAL NEAR-INFRARED SPECTROSCOPY (FNIRS) AND ELECTROENCEPHALOGRAPHY (EEG) BRAIN STATE MEASUREMENT AND FEEDBACK

(71) Applicant: HRL Laboratories, LLC, Malibu, CA (US)

(72) Inventors: Matthew E. Phillips, Calabasas, CA (US); Matthias Ziegler, Oakton, VA (US); David W. Payton, Calabasas, CA (US); Charles E. Martin, Thousand Oaks, CA (US)

(73) Assignee: HRL Laboratories, LLC, Malibu, CA (US)

(*) Notice: Subject to any disclaimer, the term of this patent is extended or adjusted under 35 U.S.C. 154(b) by 0 days.

(21) Appl. No.: 14/987,467

(22) Filed: Jan. 4, 2016

Related U.S. Application Data

(60) Provisional application No. 62/099,835, filed on Jan. 5, 2015.

(51) Int. Cl.
  *A61N 1/36* (2006.01)
  *A61B 5/16* (2006.01)
  (Continued)

(52) U.S. Cl.
  CPC ........ *A61N 1/36025* (2013.01); *A61B 5/0075* (2013.01); *A61B 5/0484* (2013.01); *A61B 5/16* (2013.01)

(58) Field of Classification Search
  CPC ................... A61N 1/36026; A61N 2011/36039
  See application file for complete search history.

(56) References Cited

U.S. PATENT DOCUMENTS

| | | | |
|---|---|---|---|
| 2015/0174418 A1* | 6/2015 | Tyler ...................... | A61B 34/10 601/2 |
| 2016/0008632 A1* | 1/2016 | Wetmore ................. | A61N 7/00 601/2 |

(Continued)

OTHER PUBLICATIONS

Merzagora, A.C., G. Foffani, I. Panyavin, L. Mordillo-Mateos, J. Aguilar, Berm Onaral, and A. Oliviero. "Prefrontal hemodynamic changes produced by anodal direct current stimulation." Neuroimage 49, No. 3 (2010): pp. 2304-2310.

(Continued)

*Primary Examiner* — Eric D. Bertram
(74) *Attorney, Agent, or Firm* — Tope-McKay & Associates

(57) ABSTRACT

Described is system for mapping user behavior to brain regions of interest. Using a cognitive-behavior model, a behavioral task is selected that is suited for a desired brain state. Using a functional-anatomical model coupled to the cognitive-behavior model, a set of high-definition neurostimulations is selected to be applied to the user during performance of the selected behavioral task. The selected set of high-definition neurostimulations targets specific regions of the user's brain. Changes in the user's brain state are sensed during application of the set of high-definition neurostimulations and performance of the selected behavioral task using at least one brain monitoring technique. The coupled functional-anatomical and cognitive-behavior models are adapted until the desired brain state is reached.

19 Claims, 11 Drawing Sheets

(51) Int. Cl.
A61B 5/0484 (2006.01)
A61B 5/00 (2006.01)

(56) References Cited

U.S. PATENT DOCUMENTS

| 2016/0038049 | A1* | 2/2016 | Geva | A61B 5/048 600/544 |
| 2016/0228702 | A1* | 8/2016 | Kempe | A61N 1/36025 |

OTHER PUBLICATIONS

Bikson, M., Rahman, A., & Datta, A. (2012). "Computational models of transcranial direct current stimulation." Clinical EEG and Neuroscience, 43(3), pp. 176-183.
Molaee-Ardekani, B., et al., (Available on line 2012). "Effects of transcranial Direct Current Stimulation (tDCS) on cortical activity: A computational modeling study," Brain Stimulation, 6, (2013), pp. 25-39.
Norman, K. A., & O'Reilly, R. C. (2003), "Modeling hippocampal and neocortical contributions to recognition memory: a complementary-learning-systems approach." Psychological review, 2003, vol. 110, No. 4, pp. 611-646.
John R Anderson, Daniel Bothell, Michael D Byrne, Scott Douglass, Christian Lebiere, and Yulin Qin. "An integrated theory of the mind." Psychological review, 2004, vol. 111, No. 4, pp. 1036-1060.
Andrea Antal and Walter Paulus. "Transcranial direct current stimulation and visual perception." Perception, 37(3): pp. 367-74, 2008.
Hasan Ayaz, MP Cakir, K Izzetoglu, Adrian Curtin, Patricia A Shewokis, Scott C Bunce, and Banu Onaral, "Monitoring expertise development during simulated uav piloting tasks using optical brain imaging." In Aerospace Conference, 2012 IEEE, pp. 1-11. IEEE, 2012.
Siwei Bei, Colleen Leo, and Socrates Dokos. A review of computational models of transcranial electrical stimulation. Critical Reviews™ in Biomedical Engineering, 41(1): pp. 21-35 (2013).
Paulo S Boggio, Roberta Ferrucci, Sergio P Rigonatti, Priscila Covre, Michael Nitsche, Alvaro Pascuat-Leone, and Felipe Fregni. "Effects of transcranial direct current stimulation on working memory in patients with parkinson's disease," Journal of the neurological sciences, 249(1): pp. 31-38, 2006.
Jeffrey J Borckardt, M. Bikson, H. Frohman, S. T Reeves, A. Datta, V. Bansal, A. Madan. K. Barth, and M. S George. "A pilot study of the tolerability and effects of high-definition transcranial direct current stimulation (hd-tdcs) on pain perception." The Journal of Pain, 13(2): pp. 112-120, 2012.
Jelmer P Borst and John R Anderson. "Using model-based functional mri to locate working memory updates and declarative memory retrievals in the fronto-parietal network." Proceedings of the National Academy of Sciences, 110 (5): pp. 1628-1633, 2013.
Angela Brunstein, Shawn Betts, and John R Anderson. "Practice enables successful learning under minimal guidance." Journal of Educational Psychology, 2009, vol. 101, No. 4, pp. 790-802.
Richard P Chi and Allan W Snyder. "Facilitate insight by, non-invasive brain stimulation," PLoS One, 6(2):e16655, 2011, pp. 1-7.
Evangelia G Chrysikou, Roy H Hamilton, H Branch Coslett, Abhishek Datta, Marom Bikson, and Sharon L. Thompson-Schill. "Noninvasive transcranial direct current stimulation over the left prefrontal cortex facilitates cognitive flexibility in tool use." Cognitive Neuroscience, (ahead-of-print): pp. 1-9, 2013.
Larry Z Daily, Marsha C Lovett, and Lynne M Reder. "Modeling individual differences in working memory performance: A source activation account." Cognitive Science, 25(3): pp. 315-353, 2001.
Abhishek Datta, Varun Bansal, Julian Diaz, Jinal Patel, Davide Reato, and Marom Bikson. "Gyri-precise head model of transcranial direct current stimulation: improved spatial focality using a ring electrode versus conventional rectangular pad", Brain stimulation, 2(4): pp. 201-207, 2009.
Abhishek Datta, Dennis Truong, Preet Minhas, Lucas C Parra, and Marom Bikson, "Inter-individual variation during transcranial direct current stimulation and normalization of dose using mri-derived computational models." Frontiers in Psychiatry, Neuropsychiatric Imagining and Stimulation, Oct. 2012, vol. 3, Article 91, pp. 1-8.
A. Data, M. Elwassif, F. Battaglia, and M. Bikson, "Transcranial current stimulation focality using disc and ring electrode configurations: Fem analysis," J Neural Eng, vol. 5, pp. 163-74, 2008.
Eran Dam, Nitzan Censor, Ethan R Buch, Marco Sandrini, and Leonardo G Cohen. "Noninvasive brain stimulation: from physiology to network dynamics and back." Nature neuroscience, 16(7): pp. 838-844, 2013.
Mario Dipoppa and Boris S Gutkin. "Flexible frequency control of cortical oscillations enables computations required for working memory." Proceedings of the National Academy of Sciences, (PNAS) Jul. 30, 2013, vol. 110, No. 31, pp. 12828-12833.
Jacek P Dmochowski, Abhishek Datta, Marom Bikson, Yuzhuo Su, and Lucas C Parra. "Optimized multi-electrode stimulation increases focatily and intensity at target." Journal of neural engineering, 8(4):046011 (16pp), 2011.
Colleen A Dockery, Ruth Hueckel-Weng, Niels Birbaumer, and Christian Plewnia. "Enhancement of planning ability by transcranial direct current stimulation." The Journal of Neuroscience, 29(22): pp. 7271-7277, 2009.
Dylan Edwards, Mar Cortes, Abhishek Data, Preet Minhas, Eric M Wassermann, and Marom Bikson. "Physiological and modeling evidence for focal transcranial electrical brain stimulation in humans: a basis for high-definition tdcs." NeuroImage 74 (2013) pp. 266-275.
Brian Falcone, Brian A Coffman, Vincent P Clark, and Raja Parasuraman. Transcranial direct current stimulation augments perceptual sensitivity and 24-hour retention in a complex threat detection task. PloS one, 7(4): 34993. 2012, pp. 1-10.
Felipe Fregni, Paulo S Boggio, Michael Nitsche, Felix Bermpohl, Andrea Antal, Eva Feredoes, Marco A Marcolin, Sergio P Rigonatti, Maria TA Silva, Walter Paulus, et al. "Anodal transcranial direct current stimulation of prefrontal cortex enhances working memory." Experimental Brain Research, 168(1): pp. 23-30, 2005.
Tobias U Hauser, Stephanie Rotzer, Roland H Grabner, Susan Mérillat. and Lutz Jäncke. "Enhancing performance in numerical magnitude processing and mental arithmetic using transcranial direct current stimulation (tdcs)." Frontiers in human neuroscience, Jun. 2013, vol. 7. Article 244, pp. 1-9.
Theodore J Huppert, Solomon G Diamond, Maria A Francesohini, and David A Boas, "Homer: a review of time-series analysis methods for near-infrared spectroscopy of the brain." Applied Optics, vol. 48, No. 10, Apr. 2009, pp. D280-D298.
Meltem Izzetogiu, Kurtuius Izzetogiu, Scott Bunce, Hasan Ayaz, Ajit Devaraj, Barer Onaral, and Kambiz Pourrezaei. "Functional near-infrared neuroimaging. Neural Systems and Rehabilitation Engineering," IEEE Transactions on, 13(2): pp. 153-159, 2005.
Susanne M Jaeggi, Martin Buschkuehl, John Jonides, and Waller J Perrig. "Improving fluid intelligence with training on working memory." Proceedings of the National Academy of Sciences, 105(19): pp. 6829-6833, 2006.
Mark Jung-Beeman, Edward M Bowden, Jason Haberman, Jennifer L Frymiare, Stella Arambel-Liu, Richard Greenblatt, Paul J Reber, and John Kounios. "Neural activity when people solve verbal problems with insight." PloS biology, Apr. 2004, vol. 2, Issue 4, pp. 0500-0510.
Juvina, Ion, Tiffany S. Jastrzembski, and R. A. McKinley. "When to apply brain stimulation to achieve learning acceleration:" In Proceedings of the International Conference on Cognitive Modeling (ICCM), pp. 358-363. 2013.
Khedr, et al., "Effect of Anodal Versus Cathodal Transcranial Direct Current Stimulation on Stroke Rehabilitation: A Pilot Randomized Controlled Trial", Neurorehabil Neural Repair, 27: pp. 592-601, 2013.
Satoru Kohne, Ichiro Miyai, Akitoshi Seiyama, Ichiro Oda, Akihiro Ishikawa, Shoichi Tsuneishi, Takashi Amite, and Koji Shimizu. "Removal of the skin blood flow artifact in functional near-infrared spectroscopic imaging data through independent component analysis" Journal of biomedical optics, 12(6): pp. 062111-1-062111-9, 2007.

(56) References Cited

OTHER PUBLICATIONS

John Kounios and Mark Beeman. "The cognitive neuroscience of insight." Annual Review of Psychology, 65(1), 2013, pp. 71-93.
John Kounios, Jessica I Fleck, Deborah L Green, Lisa Payne, Jennifer L Stevenson, Edward M Bowden, and Mark Jung-Beeman. "The origins of insight in resting-state brain activity." Neuropsychologia, 46(1): pp. 281-291, 2008.
John Kounios, Jennifer L Frymiare, Edward M Bowden, Jessica I Fleck, Karuna Subramaniam, Todd B Parrish, and Mark Jung-Beeman. "The prepared mind neural activity prior to problem presentation predicts subsequent solution by sudden insight." Psychological Science, 17(10): pp. 882-890, 2006.
Hsiao-I Kuo, Marom Bikson, Abhishek Datta, Preet Minhas, Walter Paulus, Min-Fang Kuo, and Michael A Nitsche. "Comparing cortical plasticity induced by conventional and high-definition 4× 1 ring tdcs: a neurophysiological study." Brain Stimulation, 6, (2013), pp. 644-648, (Available online Nov. 11, 2012).
Lebiere, Christian, Peter Pirnili, Robert Thomson, Jaehyon Palk, Matthew Rutledge-Taylor, James Staszewski, and John R. Anderson. "A functional model of sensemaking in a neurocognitive architecture." Computational intelligence and neuroscience, vol. 2013, (2013): Article No. 5, pp. 1-59.
Stéphanie Lefebvre, Patrice Laioux, André Peeters, Philippe Desfontaines, Jacques Jamart, and Yves Vandermeeren. "Dual-tdcs enhances online motor skill learning and long-term retention in chronic stroke patients." Frontiers in human neuroscience, Jan. 2013, vol. 6, Article 343, pp. 1 -17, (Available on line 2012).
Lehman, Jill Fain, John Laird, and Paul Rosenbloom. "A Gentle Introduction to Soar, An Architecture for Human Cognition: 2006 Update." University of Michigan (2006), pp. 1-37.
Jorge Leite, Sandra Carvalho, Felipe Fregni, and Oscar F Gonsalves. "Task-specific effects of tdcs-induced cortical excitability changes on cognitive and motor sequence set shifting performance." PloS one, Sep. 2011, vol. 6, Issue Issue 9, e24140, pp. 1-9.
Paula Sant Leon, Stuart A Knock, M Marmaduke Woodman, Lia Domide, Jochen Mersmann, Anthony R McIntosh, and Viktor Jirsa. "The Virtual Brain: a simulator of primate brain network dynamics." Frontiers in Neuroinfomiatics, Jun. 2013 vol. 7, Article 10, pp. 1-23.
Lupyan, G., Mallen, D., Hamilton, R., & Thompson-Schill, S. L. (2012). "Categorization is modulated by transcranial direct current stimulation over left prefrontal codex." Cognition, 124(1), pp. 36-49.
Oded Meiron and Michel Lavidor. "Prefrontal oscillatory stimulation modulates access to cognitive control references in retrospective metacognitive commentary," Clinical Neurophysidogy125 (2014). pages 77-82.
Monica Melby-Lervåg and Charles Hulme. "Is working memory training effective? a meta-analytic review." Developmental Psychology, 2013, vol. 49, No. 2, pp. 270-291.
Nili Metuki, Tal Sola, and Michel Lavidor. "Enhancing cognitive control components of insight problems solving by anodal tdcs of the left dorsolateral prefrontal cortex." Brain Stimulation, 5(2): pp. 110-115, 2012.
Earl K Miller and Jonathan D Cohen. "An integrative theory of prefrontal cortex function." Annual review of neuroscience, 24(1): pp. 167-202, 2001.
Behrad Noudwst and Tirin Moore, "Parietal and prefrontal neurons driven to distraction." Nature Neuroscience, 16(1); pp. 8-9, 2013.
N Nozari and S Thompson-Schill. "More attention when speaking: does it help or does it hurt?" Neuropsychologia 51 (2013), pp. 2770-2730.
Cornelia Pirulli, Anna Fertonani, and Carlo Miniussi. "The role of timing in the induction of neuromodulation in perceptual learning by transcranial electric stimulation." Brain Stimulation 6 (2013), pp. 683-669.
Albert Snowball, Ilias Tachtsidis, Tudor Popescu, Jacqueline Thompson, Margarete Delazer, Laura Zamarian, Tingting Zhu, and Roi Cohen Kadosh, "Long-term enhancement of brain function and cognition using cognitive training and brain stimulation," Current Biology 23, pp. 987-992, Jun. 3, 2013.
Surjo R Sookadar, Matthias Witkowski, Eliana G Cossio, Niels Birbaumer, Stephen E Robinson, and Leonardo G Cohen. "In vivo assessment of human brain oscillations during application of transcranial electric currents." Nature Communications (2013), 4:2032, DOI: 10.1038/ncomms3032, pp. 1-10.
R Sparing, M Mimi, MD Hesse, J Küst, H Karbe, and GR Fink, "Bidirectional alterations of interhemisphenc parietal balance by non-invasive cortical stimulation," Brain, 132(11): pp. 3011-3020, 2009.
A. Stocco and J. R. Anderson. "Endogenous controland task representation: An fmri study, in algebraic problem solving." Journal of Cognitive Neuroscience, 20(7): pp. 1300-1314, 2008.
A. Stocco, C. Lebiere, and J. R. Anderson. "Conditional routing of information to the cortex: A model of the basal ganglia's role in cognitive coordination." Psychological Review, 117(2): pp. 540-574, 2010.
Karuna Subramaniam, John Kounios, Todd B Parrish, and Mark Jung-Beeman. "A brain mechanism for facilitation of insight by positive affect," Journal of Cognitive Neuroscience, 21(3): pp. 415-432, 2009.
Dennis Q Truong, Greta Magerowski, George L Blackburn, Marom Bikson, and Miguel Alonso-Alonso, "Computational modeling of transcranial direct current stimulation (tdcs) in obesity: impact of head fat and dose guidelines." NeuroImage: Clinical 2 (2013), pp. 759-766.
Mauricio F Viliamar, Pakom Wivatvongvana, Jayanton Palumanond, Marom Bikson, Dennis Q Truong, Abhishek Datta, and Felipe Fregni. "Focal modulation of the primary motor cortex in fibromyalgia using 4× 1-ring high-definition transcranial direct current stimulation (HD-tDCS): immediate and delayed analgesic effects of cathodal and anodal stimulation." the Journal of Pain. vol. 14, No. 4 Apr. 2013: pp. 311-383.
Dieter Wallach and Christian Lebiere, "Implicit and explicit learning in a unified architecture of cognition" In Jimenez, Luis, ed. Attention and Implicit Learning.. Philadelphia, PA, USA: John Benjamins Publishing Company, 2003, pp. 215-250.
Javadi, A. H., & Walsh, V. (2012). "Transcranial direct current stimulation (tDCS) of the left dorsolateral prefrontal cortex modulates declarative memory." Brain Stimulation, 5(3), pp. 231-241.
Patterson, Freda, Christopher Jepson, Andrew A. Strasser, James Loughead, Kenneth A. Perkins, Ruben C. Gur, Joseph M. Frey. Steven Siegel, and Caryn Lerman. "Varenicline improves mood and cognition during smoking abstinence." Biological Psychiatry 65. No. 2 (2009): pp. 144-149.
Ahmed, Amir IA, Abduliah NA Ali Cees Kramers, Linde VD Härmark, David M. Burger; and Willem MA Verhoeven. "Neuropsychiatric adverse events of varenicline: a systematic review of published reports" Journal of Clinical Psychopharmacology 33, No. 1 (2013): pp. 55-62.
Zwissler, B., et al., "Shaping memory accuracy by left prefrontal transcranial direct current stimulation," The Journal of Neuroscience, 34(11), pp. 4022-4026, 2014.
Sparing, R., Thimm, M., Hesse, M.D., Mist, J., Karbe, H., and Fink, G.R. (2009). Bidirectional alterations of interhemispheric parietal balance by non-invasive cortical stimulation. Brain, 132, 11: pp. 3011-3020.
Stocco, A. and Anderson, J.R. (2008). Endogenous control and task representation: An fmri study in algebraic problem solving. Journal of Cognitive Neuroscience, 20, 7: pp. 1300-1314.
Stocco, A., Lebiere, C., and Anderson, J.R. (2010). Conditional routing of information to the cortex: A model of the basal ganglia's role in cognitive coordination. Psychological Review, 117, 2: pp. 540-574.
Subramaniam, K., Kounios, J., Parrish, T.B., and Jung-Beeman, M. (2009). A brain mechanism for facilitation of insight by positive affect. Journal of Cognitive Neuroscience, 21, 3: pp. 415-432.
Truong, D.Q., Magerowski, G., Blackburn, G.L., Bikson, and Alonso-Alonso, M. (2013) Computational modeling of transcranial direct current stimulation (tdcs) in obesity: impact of head fat and dose guidelines. NeuroImage: Clinical 2, pp. 759-766.

(56) References Cited

OTHER PUBLICATIONS

Villamar, M.F., Wivatvongvana, P., Patumanond, J., Bikson, M., Truong, D.Q., Datta, A., and Fregni, F. (2013). Focal modulation of the primary motor cortex in fibromyalgia using 4× 1-ring high-definition transcranial direct current stimulation (HD-tDCS): immediate and delayed analgesic effects of cathodal and anodal stimulation. The Journal of Pain, pp. 371-383.

Wallach, D. and Lebiere, C. (2003). Implicit and explicit learning in a unified architecture of cognition, In L. Jimenez, editor, Attention and Implicit Learning. John Benjamins, Amsterdam, Netherlands, pp. 215-250.

Javadi, A. H., & Walsh, V. (2012). Transcranial direct current stimulation (tDCS) of the left dorsolateral prefrontal cortex modulates declarative memory. Brain Stimulation, 5(3), pp. 231-241.

Patterson, F., Jepson, C., Strasser, a.a., Loughead, J., Perkins, K.A., Gur, R.C., Frey, J.M., Siegel, S., and Lerman, C. (2009). Varenicline improves mood and cognition during smoking abstinence. Biological Psychiatry, 65, 2: pp. 144-149.

Ahmed, Amir, IA, Ali, A., Kramers, C., Harmark, L., Burger, D.M., and Verhoeven, W. (2013). Neuropsychiatric adverse events of varenicline: a systematic review of published reports. Journal of Clinical Psychopharmacology, 33, 1: pp. 55-62.

Haddal & Gertler. (2010) Homeland Security: Unmanned Aerial Vehicles and Boarder Surveillance. Congressional Research Service Report for Congress. pp. 1-7.

Attrition: Pilots Despise Flying UAVs. h t t p :/ /w w w . strategypage.com/htmw/htatrit/articles/20120812.aspx. Taken on Apr. 14, 2016.

No One Wants to be a Drone Pilot, U.S. Air Force Discovers. h t t p :/ /w w w .popsci.com/technology/article/2013-08/air-force-drone-program-too-unmanned-its-own-good. Taken on Apr. 14, 2016.

Performance Management. h t t p :/ /w w w .opm.gov/policy-data-oversight/performance-management/reference-materials/historical/facts-about-measuring-team-performance. Taken on Apr. 14, 2016.

Konvalinka, I., & Roepstorff, A. (2012). The two-brain approach: how can mutually interacting brains teach us something about social interaction? Frontiers in Human Neuroscience, 6, pp. 1-10.

Bell, Anthony J., and Terrence J. Sejnowski. (1995). "An information-maximization approach to blind separation and blind deconvolution." Neural computation 7, No. 6: pp. 1129-1159.

http://en.wikipedia.org/wiki/AAI_RQ-7_Shadow Downloaded on Oct. 24, 2016.

Robert J Sternberg and Janet E Davidson. The nature of insight. The MIT Press, 1995. Chapter 6: 6. Cognitive and Affective Components of Insight, pp. 197-226.

Merzagora, A. C., Foffani, G., Panyavin I., Mordillo-Mateos, L., Aguilar, J., Onaral, B. and A. Oliviero. (2010). Prefrontal hemodynamic changes produced by anodal direct current stimulation. Neuroimage, 49, 3: pp. 2304-2310.

Bikson, M., Rahman, A., and Datta, A. (2012). Computational models of transcranial direct current stimulation. Clinical EEG and Neuroscience, 43, 3: pp. 176-183.

Molaee-Ardekani, B., Marquez-Ruiz, J., Merlet, I., Leal-Campanario, R., Gruart, A., Sánchez-Campusano, R., and Wendling, F. (2012). Effects of transcranial Direct Current Stimulation (tDCS) on cortical activity: A computational modeling study. Brain stimulation. pp. 25-39.

Norman, K. A. and O'Reilly, R. C. (2003). Modeling hippocampal and neocortical contributions to recognition memory: a complementary-learning-systems approach. Psychological review, 110, 4: pp. 611-646.

Anderson, J. R., Bothell, D., Byrne, M. D., Douglass, S., Lebiere, C., and Qin, Y. (2004). An integrated theory of the mind. Psychological review, 111, 4: pp. 1036-1060.

Antal, A. and Paulus, W. (2008). Transcranial direct current stimulation and visual perception. Perception, 37, 3: pp. 367-374.

Hasan Ayaz, M.P., Cakir, K., Izzetoglu, Curtin, A., Shewokis, P.A., Bunce S. C., and Onaral, B. (2012). Monitoring expertise development during simulated uav piloting tasks using optical brain imaging. Aerospace Conference. 2012 IEEE, pp. 1-11.

Siwei, Bai, Loo, C. and Dokos. S. A review of computational models of transcranial electrical stimulation. (2013). Critical Reviews™ in Biomedical Engineering, pp. 21-35.

Boggio, P.S., Ferrucci, R., Rigonafii, S.P., Covre, P., Nitsche, M., Pascual-Leone, A., and Fregni, F. (2006). Effects of transcranial direct current stimulation on working memory in patients with parkinson's disease. Journal of the neurological sciences, 249, 1: pp. 31-38.

Borckardt, J.J., Bikson, M., Frohman, H., Reeves, S. T., Datta, A., Bansal, V., Madan, A., Barth, K., and George, M. S. (2012). A pilot study of the tolerability and effects of high-definition transcranial direct current stimulation (hd-tdcs) on pain perception. The Journal of Pain, 13, 2: pp. 112-120.

Borst, J. P. and Anderson, J.R. (2013). Using model-based functional mri to locate working memory updates and declarative memory retrievals in the fronto-parietal network. Proceedings of the National Academy of Sciences, 110, 5: pp. 1628-1633.

Brunstein, A., Betts, S., and Anderson, J.A. (2009). Practice enables successful learning under minimal guidance. Journal of Educational Psychology, 101, 4: pp. 790-802.

Chi, R.P. and Snyder, A.W. (2011). Facilitate insight by non-invasive brain stimulation. PLoS One, 6, 2:e16655, pp. 1-7.

Chrysikou, E.G., Hamilton, R.H., Coslett, H.B., Datta, A., Bikson, M., and Thompson-Schill, S.L. (2013). Noninvasive transcranial direct current stimulation over the left prefrontal cortex facilitates cognitive flexibility in tool use. Cognitive Neuroscience, (ahead-of-print): pp. 1-9.

Daily, L.Z., Lovett, M.C., and Reder, L.M. (2001). Modeling individual differences in working memory performance: A source activation account. Cognitive Science, 25, 3: pp. 315-353.

Datta, A., Bansal, V., Diaz, J., Patel, J., Reato, D., and Bikson, M. (2009). Gyri-precise head model of transcranial direct current stimulation: improved spatial focality using a ring electrode versus conventional rectangular pad. Brain stimulation, 2, 4: pp. 201-207.

Datta, A., Truong, D., Minhas. P., Parra, L.C., and Bikson, M. (2012). Inter-individual variation during transcranial direct current stimulation and normalization of dose using mri-derived computational models. Frontiers in Psychiatry, 3, pp. 1-8.

Dayan, E., Censor, N., Buch, E.R., Sandrini, M., and Cohen, L.G. (2013). Noninvasive brain stimulation: from physiology to network dynamics and back. Nature neuroscience, 16, 7: pp. 838-844.

Dipoppa, M. and Gutkin, B.S. (2013). Flexible frequency control of cortical oscillations enables computations required for working memory. Proceedings of the National Academy of Sciences, pp. 12828-12833.

Dmochowski, J.P., Datta, A., Bikson, M., Su, Y., and Parra, L.C. (2011). Optimized multi-electrode stimulation increases focality and intensity at target. Journal of neural engineering, 8, 4:046011, pp. 1-16.

Dockery, C.A., Hueckel-Weng, R., Birbaumer, N., and Plewnia, C. (2009). Enhancement of planning ability by transcranial direct current stimulation. The Journal of Neuroscience, 29, 22: pp. 7271-7277.

Edwards, D., Cortes, M., Datta, A., Minhas, P., Wassermann, E. M., and Bikson, M. (2013). Physiological and modeling evidence for focal transcranial electrical brain stimulation in humans: a basis for high-definition tdcs. NeuroImage, pp. 266-275.

Falcone, B., Coffman, B.A., Clark, V.P., and Parasuraman, R. (2012). Transcranial direct current stimulation augments perceptual sensitivity and 24-hour retention in a complex threat detection task. PloS one, 7, 4:e34993, pp. 1-10.

Fregni, F., Boggio, P.S., Nitsche, M., Bermpohl, F., Antal, A., Feredoes, E., Marcolin, M.A., Rigonatti, S.P., Silva, M.T.A., Paulus, W., et al. (2005). Anodal transcranial direct current stimulation of prefrontal cortex enhances working memory. Experimental Brain Research, 166, 1: pp. 23-30.

Hauser, T.U., Rotzer, S., Grabner, R.H., Merillat, S., and Jäncke, L. (2013). Enhancing performance in numerical magnitude processing and mental arithmetic using transcranial direct current stimulation (tdcs). Frontiers in human neuroscience, 7, pp. 1-9.

(56) References Cited

OTHER PUBLICATIONS

Huppert, T.J., Diamond, S.G., Franceschini, M.A., and Boas, D.A. (2009). Homer: a review of time-series analysis methods for near-infrared spectroscopy of the brain. Applied optics, 48, 10: pp. D280-D298.

Izzetoglu, M., Izzetoglu, K., Bunce, S., Ayaz, H., Devaraj, A., Onaral, B., and Pourrezaei, K. (2005). Functional near-nfrared neuroimaging. Neural Systems and Rehabilitation Engineering, IEEE Transactions on, 13, 2: pp. 153-159.

Jaeggi, S.M., Buschkuehl, M., Jonides, J., and Perrig, W.J. (2008). Improving fluid intelligence with training on working memory. Proceedings of the National Academy of Sciences, 105, 19: pp. 6829-6833.

Jung-Beeman, M., Bowden, E.M., Haberman, J., Frymiare, J.L., Arambel-Liu, S., Greenblatt, R., Reber, P.J., and Kounios, J. (2004). Neural activity when people solve verbal problems with insight. PLoS biology, 2, 4:e97, pp. 0500-1-0500-11.

Juvina, I., Jastrzembski, T.S., and McKinley, A. "When to apply brain stimulation to achieve learning acceleration," ICCM Conference 2013, pp. 358-363.

Kohno, S., Miyai, I., Seiyama, A., Oda, I., Ishikawa, A., Tsuneishi, S., Takashi Amita, T., and Shimizu, K. (2007). Removal of the skin blood flow artifact in functional near-infrared spectroscopic imaging data through independent component analysis. Journal of biomedical optics, 12, 6:062111-1-062111-9.

Kounios, J. and Beeman, M. (2013). The cognitive neuroscience of insight. Annual Review of Psychology, 65, 1, pp. 210-216.

Kounios, J., Fleck, J.I. Green, D.L. Payne, L., Stevenson, J.L., Bowden, E.M., and Jung-Beeman, M. (2008). The origins of insight in resting-state brain activity. Neuropsychologia, 46, 1: pp. 281-291.

Kounios, J., Frymiare, J.L., Bowden, E.M., Fleck, J.I., Subramaniam, K., Parrish, T.B., and Jung-Beeman, M. (2006). The prepared mind neural activity prior to problem presentation predicts subsequent solution by sudden insight. Psychological Science, 17, 10: pp. 882-890.

Kuo, H-I., Bikson, M., Datta, A., Minhas, P., Paulus, W., Kuo, M-F., and Nitsche, M.A. (2012). Comparing cortical plasticity induced by conventional and high-definition 4+ 1 ring tdcs: a neurophysiological study. Brain stimulation, pp. 644-648.

Lebiere, C., Pirolli, P., Thomson, R., Paik, J., Rutledge-Taylor, M., James Staszewski, and Anderson, J.R. (2013). A functional model of sensemaking in a neurocognitive architecture. Computational Intelligence and Neuroscience, 2013: e921695, pp. 1-29.

Lefebvre, S., Laloux, P., Peeters, A., Desfontaines, P., Jamart, J., and Vandermeeren, Y. (2012). Dual-tdcs enhances online motor skill learning and long-term retention in chronic stroke patients. Frontiers in human neuroscience, 6, pp. 1-17.

Lehman, J., Laird, J., and Rosenbloom, P. (2006). A gentle introduction to soar, an architcture for human cognition, pp. 1-47.

Leite, J., Carvalho, S., Fregni, F., and Gonsalves, O.F. (2011). Task-specific effects of tdcs-induced cortical excitability changes on cognitive and motor sequence set shifting performance. PloS one, 6, 9:e24140, pp. 1-9.

Leon, P.S., Knock, S.A., Woodman, M.M., Domide, L., Mersmann, J., McIntosh, A.R., and Jirsa, V. (2013). The Virtual Brain: a simulator of primate brain network dynamics. Frontiers in Neuroinformatics, 7, pp. 1-23.

Lupyan, G., Mirman, D., Hamilton, R., & Thompson-Schill, S. L. (2012). Categorization is modulated by transcranial direct current stimulation over left prefrontal cortex. Cognition, 124, 1: pp. 36-49.

Meiron, O. and Lavidor, M. (2013). Prefrontal oscillatory stimulation modulates access to cognitive control references in retrospective metacognitive commentary. Clinical Neurophysiology, pp. 77-82.

Melby-Lervåg, M. and Hulme, C. (2013). Is working memory training effective? a meta-analytic review. Developmental Psychology, 49, 2:pp. 270-291.

Metuki, N., Sela, T., and Lavidor, M. (2012). Enhancing cognitive control components of insight problems solving by modal tdcs of the left dorsolateral prefrontal corte. Brain Stimulation, 5, 2: pp. 110-115.

Miller, E. K. and Cohen, J.D. (2001). An integrative theory of prefrontal cortex function. Annual review of neuroscience, 24, 1: pp. 167-202.

Noudoost, B. and Moore, T. (2013). Parietal and prefrontal neurons driven to distraction. Nature Neuroscience, 16, 1: pp. 8-9.

Nozari, N. and Thompson-Schill, S. (2013). More attention when speaking: does it help or does it hurt?, Neuropsychologia 51, pp. 2770-2780.

Pirulli, C., Fertonani, A., and Miniussi, C. (2013). The role of timing in the induction of neuromodulation in perceptual learning by transcranial electric stimulation. Brain stimulation 6, pp. 683-689.

Snowball, A., Tachtsidis, I., Popescu, T., Thompson, J., Delazer, M., Zamarian, L., Zhu, T., and Kadosh, R. C. (2013). Long-term enhancement of brain function and cognition using cognitive training and brain stimulation. Current Biology 23, pp. 987-992.

Soekadar, S.R., Witkowski, M., Cossio, E.G., Birbaumer, N., Robinson, S.E., and Cohen, L.G. (2013). In vivo assessment of human brain oscillations during application of transcranial electric currents. Nature Communications, 4, pp. 1-10.

\* cited by examiner

THINKING CAP: COMBINING PERSONALIZED, MODEL-DRIVEN, AND ADAPTIVE HIGH DEFINITION TRANS-CRANIAL STIMULATION (HD-TCS) WITH FUNCTIONAL NEAR-INFRARED SPECTROSCOPY (FNIRS) AND ELECTROENCEPHALOGRAPHY (EEG) BRAIN STATE MEASUREMENT AND FEEDBACK

CROSS-REFERENCE TO RELATED APPLICATIONS

This is a Non-Provisional Application of U.S. Provisional Application No. 62/099,835, filed in the United States on Jan. 5, 2015, entitled, "The Thinking Cap: Combining Personalized, Model-Driven, and Adaptive HD-tCS with fNIRs and EEG Brain State Measurement and Feedback," which is incorporated herein by reference in its entirety.

BACKGROUND OF INVENTION

(1) Field of Invention

The present invention relates to a system for mapping user behavior to brain regions of interest and, more particularly, to a system for mapping user behavior to brain regions of interest using a combination of cognitive-behavioral and functional-anatomical modeling.

(2) Description of Related Art

Neurostimulation has been recently developed as a viable tool for: cognitive training and enhancement, rapid recovery from brain injury including stroke, traumatic-brain-injuries, and as a teaching and learning assistance tool. However, while a number of experiments have demonstrated performance enhancement due to various forms of neurostimulation interventions, most studies show high variability and a tendency for some users to do worse even though the overall performance of the user pool improves (see the List of Incorporated Literature References, Literature Reference No. 47).

Current methods of cognitive enhancing neurostimulation have been limited by task specific improvements, a lack of personalization and adaptation, and a limited understanding of mechanistic changes. These methods have shown only limited applicability and transition potential to working environments.

Other methods use anatomical models, such as those described in Literature Reference Nos. 2 and 3, to direct neurostimulation, but cannot make predictions of human or animal cognitive behaviors based on neurobiological mechanisms through lesion studies or neurotransmitter imbalances (see Literature Reference No. 4).

Thus, a continuing need exists for a system that will personalize and adapt neurostimulations to pinpoint the phenotypic neurobiological mechanisms across a large population with a variety of neural imaging methods.

SUMMARY OF THE INVENTION

The present invention relates to a system for mapping user behavior to brain regions of interest and, more particularly, to a system for mapping user behavior to brain regions of interest using a combination of cognitive-behavioral and functional-anatomical modeling. The system comprises one or more processors and a memory having instructions such that when the instructions are executed, the one or more processors perform multiple operations. Using a functional-anatomical model coupled to a cognitive-behavior model, a set of high-definition neurostimulations is selected, wherein the selected set of high-definition neurostimulations targets specific regions of the user's brain. Conditions in the user's brain state are sensed during application of the set of high-definition neurostimulations and performance of a selected behavioral task using at least one brain monitoring technique. The coupled functional-anatomical and cognitive-behavior models are adapted until the desired brain state is reached.

In another aspect, a set of behavioral performance deficiencies in the user is assessed. The set of behavioral performance deficiencies are associated with brain states in various brain regions of the user. The user is analyzed with a neuroimaging device as the user performs a plurality of behavioral tasks, wherein the user's performance is used to parameterize the cognitive-behavior model. The cognitive-behavior model is implemented in a cognitive simulator. The cognitive-behavior model is used to predict the user's performance for a plurality of related behavioral tasks. The cognitive-behavior model is used to generate the set of behavioral tasks. For each task, the set of behavioral tasks is searched for the desired brain state for the user.

In another aspect, the functional-anatomical model is used to associate brain regions of the user for the desired brain state to specific physical locations within the skull of the user. The functional-anatomical model is used to select the set of high-definition neurostimulations to be applied to reach the associated brain regions of the user effectively to induce the desired brain state.

In another aspect, the cognitive-behavior model is used to assess changes in the user's brain state as the user performs the selected behavioral task. A new behavioral task in the set of behavioral tasks is output for the user to perform.

In another aspect, the cognitive-behavior model is used to identify specific regions of the user's brain to be targeted with a selected set of high-definition neurostimulations during performance of the new behavioral task based on a previous brain state of the user.

In another aspect, two brain monitoring techniques are used to sense changed in the user's brain state, wherein the first brain monitoring technique is electoencephalography (EEG) to monitor brain activity in an anterior cingulate region of the user's brain, and wherein the second brain monitoring technique is functional near-infrared spectroscopy (fNIRS) to monitor brain activity in a prefrontal cortex region of the user's brain.

In another aspect, the system selects using a cognitive-behavior model, a behavioral task from a set of behavioral tasks that is suited for a desired brain state.

In another aspect, the system applies the set of high-definition neurostimulations to the user during performance of the selected behavioral task.

In another aspect, the present invention also comprises a method for causing a processor to perform the operations described herein and performing the listed operations.

Finally, in yet another aspect, the present invention also comprises a computer program product comprising computer-readable instructions stored on a non-transitory computer-readable medium that are executable by a computer having a processor for causing the processor to perform the operations described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
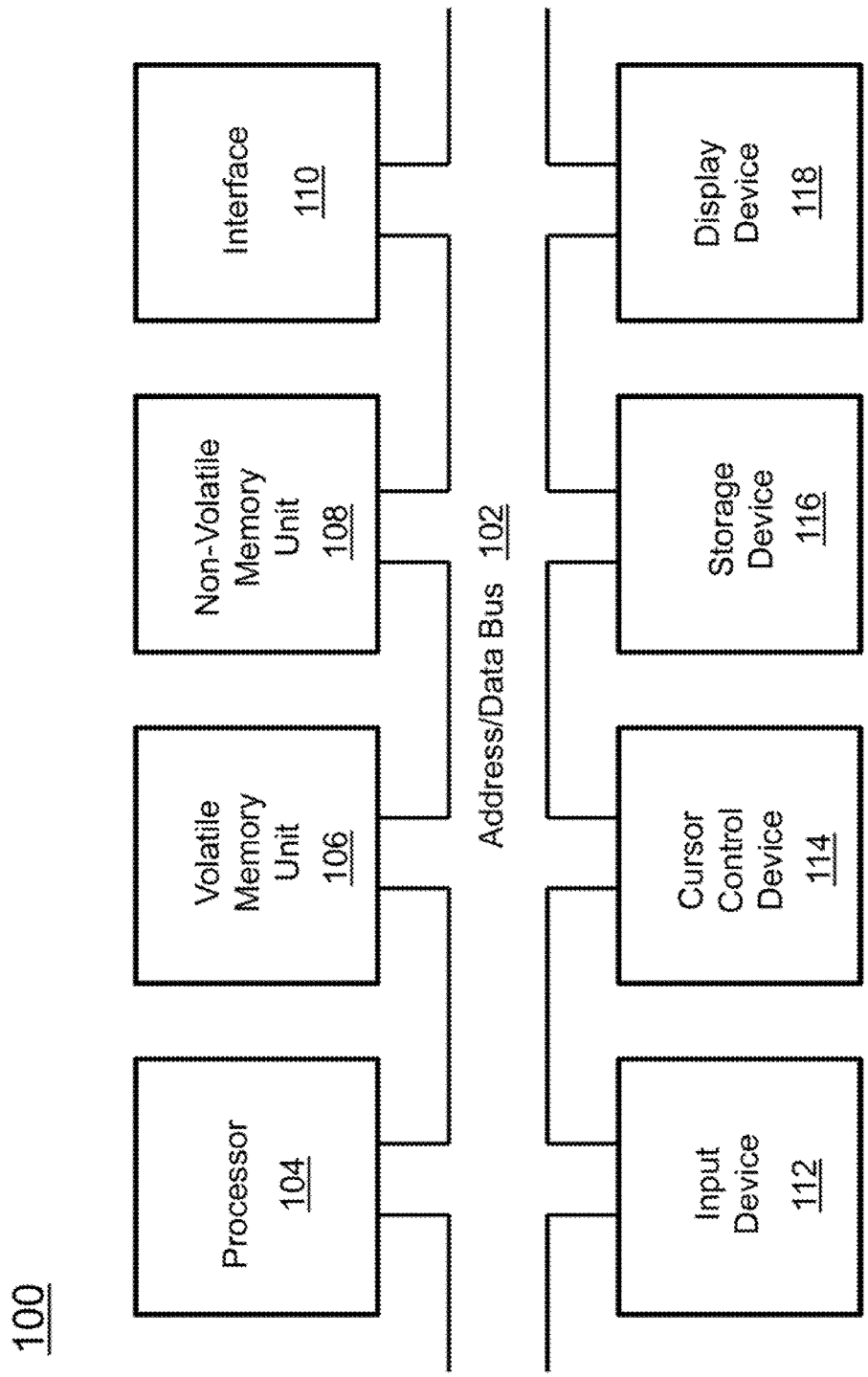
FIG. 1 is a block diagram depicting the components of a system for mapping user behavior to brain regions of interest according to some embodiments of the present disclosure.

The present invention relates to a system for mapping user behavior to brain regions of interest and, more particularly, to a system for mapping user behavior to brain regions of interest using a combination of cognitive-behavioral and functional-anatomical modeling. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter-clockwise have been used for convenience purposes only and are not intended to imply any particular fixed direction. Instead, they are used to reflect relative locations and/or directions between various portions of an object. As such, as the present invention is changed, the above labels may change their orientation.

Before describing the invention in detail, first a list of incorporated literature references as used in the description is provided. Next, a description of various principal aspects of the present invention is provided. Following that is an introduction that provides an overview of the present invention. Finally, specific details of the present invention are provided to give an understanding of the specific aspects.

(1) LIST OF INCORPORATED LITERATURE REFERENCES

The following references are incorporated and cited throughout this application. For clarity and convenience, the references are listed herein as a central resource for the reader. The following references are hereby incorporated by reference as though fully included herein. The references are cited in the application by referring to the corresponding literature reference number, as follows:

1. Merzagora, Anna C., G. Foffani, I. Panyavin, L. Mordillo-Mateos, J. Aguilar, Banu Onaral, and A. Oliviero. "Prefrontal hemodynamic changes produced by anodal direct current stimulation." Neuroimage 49, no. 3 (2010): 2304-2310.
2. Bikson, M., Rahman, A., & Datta, A. (2012). Computational models of transcranial direct current stimulation. Clinical EEG and Neuroscience, 43(3), 176-183.
3. Molaee-Ardekani, B., Márquez-Ruiz, J., Merlet, I., Leal-Campanario, R., Gruart, A., Sánchez-Campusano, R., & Wendling, F. (2012). Effects of transcranial Direct Current Stimulation (tDCS) on cortical activity: A computational modeling study. Brain stimulation.
4. Norman, K. A., & O'Reilly, R. C. (2003). Modeling hippocampal and neocortical contributions to recognition memory: a complementary-learning-systems approach. Psychological review, 110(4), 611.
5. John R Anderson, Daniel Bothell, Michael D Byrne, Scott Douglass, Christian Lebiere, and Yulin Qin. An integrated theory of the mind. Psychological review, 111(4):1036, 2004.
6. Andrea Antal and Walter Paulus. Transcranial direct current stimulation and visual perception. Perception, 37(3):367-74, 2008.
7. Hasan Ayaz, M P Cakir, K Izzetoglu, Adrian Curtin, Patricia A Shewokis, Scott C Bunce, and Banu Onaral. Monitoring expertise development during simulated UAV piloting tasks using optical brain imaging. In Aerospace Conference, 2012 IEEE, pages 1-11. IEEE, 2012.

8. Siwei Bai, Colleen Loo, and Socrates Dokos. A review of computational models of transcranial electrical stimulation. Critical Reviews™ in Biomedical Engineering, 2013.
9. Paulo S Boggio, Roberta Ferrucci, Sergio P Rigonatti, Priscila Covre, Michael Nitsche, Alvaro Pascual-Leone, and Felipe Fregni. Effects of transcranial direct current stimulation on working memory in patients with parkinson's disease. Journal of the neurological sciences, 249 (1):31-38, 2006.
10. Jeffrey J Borckardt, Marom Bikson, Heather Frohman, Scott T Reeves, Abhishek Datta, Varun Bansal, Alok Madan, Kelly Barth, and Mark S George. A pilot study of the tolerability and effects of high-definition transcranial direct current stimulation (hd-tdcs) on pain perception. The Journal of Pain, 13(2): 112-120, 2012.
11. Jelmer P Borst and John R Anderson. Using model-based functional MRI to locate working memory updates and declarative memory retrievals in the fronto-parietal network. Proceedings of the National Academy of Sciences, 110(5):1628-1633, 2013.
12. Angela Brunstein, Shawn Betts, and John R Anderson. Practice enables successful learning under minimal guidance. Journal of Educational Psychology, 101(4):790, 2009.
13. Richard P Chi and Allan W Snyder. Facilitate insight by non-invasive brain stimulation. PLoS One, 6(2):e16655, 2011.
14. Evangelia G Chrysikou, Roy H Hamilton, H Branch Coslett, Abhishek Datta, Marom Bikson, and Sharon L Thompson-Schill. Noninvasive transcranial direct current stimulation over the left prefrontal cortex facilitates cognitive flexibility in tool use. Cognitive Neuroscience, (ahead-of-print): 1-9, 2013.
15. Larry Z Daily, Marsha C Lovett, and Lynne M Reder. Modeling individual differences in working memory performance: A source activation account. Cognitive Science, 25(3):315-353, 2001.
16. Abbishek Datta, Varun Bansal, Julian Diaz, Jinal Patel, Davide Reato, and Marom Bikson. Gyri-precise head model of transcranial direct current stimulation: improved spatial focality using a ring electrode versus conventional rectangular pad. Brain stimulation, 2(4):201-207, 2009.
17. Abhishek Datta, Dennis Truong, Preet Minhas, Lucas C Parra, and Marom Bikson. Inter-individual variation during transcranial direct current stimulation and normalization of dose using mri-derived computational models. Frontiers in Psychiatry, 3, 2012.
18. Eran Dayan, Nitzan Censor, Ethan R Buch, Marco Sandrini, and Leonardo G Cohen. Noninvasive brain stimulation: from physiology to network dynamics and back. Nature neuroscience, 16(7):838-844, 2013.
19. Mario Dipoppa and Boris S Gutkin. Flexible frequency control of cortical oscillations enables computations required for working memory. Proceedings of the National Academy of Sciences, 2013.
20. Jacek P Dmochowski, Abhishek Datta, Marom Bikson, Yuzhuo Su, and Lucas C Parra. Optimized multi-electrode stimulation increases focality and intensity at target. Journal of neural engineering, 8(4):046011, 2011.
21. Colleen A Dockery, Ruth Hueckel-Weng, Niels Birbaumer, and Christian Plewnia. Enhancement of planning ability by transcranial direct current stimulation. The Journal of Neuroscience, 29(22):7271-7277, 2009.
22. Dylan Edwards, Mar Cortes, Abhishek Datta, Preet Minhas, Eric M Wassermann, and Marom Bikson. Physiological and modeling evidence for focal transcranial electrical brain stimulation in humans: a basis for high-definition tdcs. NeuroImage, 2013.
23. Brian Falcone, Brian A Coffman, Vincent P Clark, and Raja Parasuraman. Transcranial direct current stimulation augments perceptual sensitivity and 24-hour retention in a complex threat detection task. PloS one, 7(4):e34993, 2012.
24. Felipe Fregni, Paulo S Boggio, Michael Nitsche, Felix Bermpohl, Andrea Antal, Eva Feredoes, Marco A Marcolin, Sergio P Rigonatti, Maria T A Silva, Walter Paulus, et al. Anodal transcranial direct current stimulation of prefrontal cortex enhances working memory. Experimental Brain Research, 166(1):23-30, 2005.
25. Tobias U Hauser, Stephanie Rotzer, Roland H Grabner, Susan Mérillat, and Lutz Jäncke. Enhancing performance in numerical magnitude processing and mental arithmetic using transcranial direct current stimulation (tdcs). Frontiers in human neuroscience, 7, 2013.
26. Theodore J Huppert, Solomon G Diamond, Maria A Franceschini, and David A Boas. Homer: a review of time-series analysis methods for near-infrared spectroscopy of the brain. Applied optics, 48(10):D280-D298, 2009.
27. Meltem Izzetoglu, Kurtulus Izzetoglu, Scott Bunce, Hasan Ayaz, Ajit Devaraj, Banu Onaral, and Kambiz Pourrezaei. Functional near-infrared neuroimaging. Neural Systems and Rehabilitation Engineering, IEEE Transactions on, 13(2):153-159, 2005.
28. Susanne M Jaeggi, Martin Buschkuehl, John Jonides, and Walter J Perrig. Improving fluid intelligence with training on working memory. Proceedings of the National Academy of Sciences, 105(19):6829-6833, 2008.
29. Mark Jung-Beeman, Edward M Bowden, Jason Haberman, Jennifer L Frymiare, Stella Arambel-Liu, Richard Greenblatt, Paul J Reber, and John Kounios. Neural activity when people solve verbal problems with insight. PLoS biology, 2(4):e97, 2004.
30. Ion Juvina, Tiffany S Jastrzembski, and Andy McKinley. When to apply brain stimulation to achieve learning acceleration.
31. Satoru Kohno, Ichiro Miyai, Akitoshi Seiyama, Ichiro Oda, Akihiro Ishikawa, Shoichi Tsuneishi, Takashi Amita, and Koji Shimizu. Removal of the skin blood flow artifact in functional near-infrared spectroscopic imaging data through independent component analysis. Journal of biomedical optics, 12(6):062111-062111, 2007.
32. John Kounios and Mark Beeman. The cognitive neuroscience of insight. Annual Review of Psychology, 65(1), 2013.
33. John Kounios, Jessica I Fleck, Deborah L Green, Lisa Payne, Jennifer L Stevenson, Edward M Bowden, and Mark Jung-Beeman. The origins of insight in resting-state brain activity. Neuropsychologia, 46(1):281-291, 2008.
34. John Kounios, Jennifer L Frymiare, Edward M Bowden, Jessica I Fleck, Karuna Subramaniam, Todd B Parrish, and Mark Jung-Beeman. The prepared mind neural activity prior to problem presentation predicts subsequent solution by sudden insight. Psychological Science, 17(10):882-890, 2006.
35. Hsiao-I Kuo, Marom Bikson, Abhishek Datta, Preet Minhas, Walter Paulus, Min-Fang Kuo, and Michael A Nitsche. Comparing cortical plasticity induced by conventional and high-definition 4×1 ring tdcs: a neurophysiological study. Brain stimulation, 2012.
36. Christian Lebiere, Peter Pirolli, Robert Thomson, Jaehyon Paik, Matthew Rutledge-Taylor, James Staszewski, and John R Anderson. A functional model of sensemaking 37. Stephanie Lefebvre, Patrice Laloux, André Peeters, Philippe Desfontaines, Jacques Jamart, and Yves Vandermeeren. Dual-tdcs enhances online motor skill learning and long-term retention in chronic stroke patients. Frontiers in human neuroscience, 6, 2012.
38. J Lehman, John Laird, and Paul Rosenbloom. A gentle introduction to soar, an architecture for human cognition: 2006 update, 2007.
39. Jorge Leite, Sandra Carvalho, Felipe Fregni, and Oscar F Gonçalves. Task-specific effects of tdcs-induced cortical excitability changes on cognitive and motor sequence set shifting performance. PloS one, 6(9):e24140, 2011.
40. Paula Sanz Leon, Stuart A Knock, M Marmaduke Woodman, Lia Domide, Jochen Mersmann, Anthony R McIntosh, and Viktor Jirsa. The Virtual Brain: a simulator of primate brain network dynamics. Frontiers in Neuroinformatics, 7, 2013.
41. Lupyan, G., Mirman, D., Hamilton, R., & Thompson-Schill, S. L. (2012). Categorization is modulated by transcranial direct current stimulation over left prefrontal cortex. Cognition, 124(1), 36-49.
42. Oded Meiron and Michal Lavidor. Prefrontal oscillatory stimulation modulates access to cognitive control references in retrospective metacognitive commentary. Clinical Neurophysiology, 2013.
43. Monica Melby-Lervåg and Charles Hulme. Is working memory training effective? a meta-analytic review. Developmental Psychology, 49(2):270, 2013.
44. Nili Metuki, Tal Sela, and Michal Lavidor. Enhancing cognitive control components of insight problems solving by anodal tdcs of the left dorsolateral prefrontal cortex. Brain Stimulation, 5(2):110-115, 2012.
45. Earl K Miller and Jonathan D Cohen. An integrative theory of prefrontal cortex function. Annual review of neuroscience, 24(1): 167-202, 2001.
46. Behrad Noudoost and Tirin Moore. Parietal and prefrontal neurons driven to distraction. Nature Neuroscience, 16(1):8-9, 2013.
47. N Nozari and S Thompson-Schill. More attention when speaking: does it help or does it hurt? 2013.
48. Cornelia Pirulli, Anna Fertonani, and Carlo Miniussi. The role of timing in the induction of neuromodulation in perceptual learning by transcranial electric stimulation. Brain stimulation, 2013.
49. Albert Snowball, Ilias Tachtsidis, Tudor Popescu, Jacqueline Thompson, Margarete Delazer, Laura Zamarian, Tingting Zhu, and Roi Cohen Kadosh. Long-term enhancement of brain function and cognition using cognitive training and brain stimulation. Current Biology, 2013.
50. Surjo R Soekadar, Matthias Witkowski, Eliana G Cossio, Niels Birbaumer, Stephen E Robinson, and Leonardo G Cohen. In vivo assessment of human brain oscillations during application of transcranial electric currents. Nature Communications, 4, 2013.
51. R Sparing, M Thimm, M D Hesse, J Küst, H Karbe, and G R Fink. Bidirectional alterations of interhemispheric parietal balance by non-invasive cortical stimulation. Brain, 132(11):3011-3020, 2009.
52. Robert J Sternberg and Janet E Davidson. The nature of insight. The MIT Press, 1995.
53. A. Stocco and J. R Anderson. Endogenous control and task representation: An fmri study in algebraic problem solving. Journal of Cognitive Neuroscience, 20(7): 1300-1314, 2008.
54. A. Stocco, C. Lebiere, and J. R. Anderson. Conditional routing of information to the cortex: A model of the basal ganglia's role in cognitive coordination. Psychological Review, 117(2):540-574, 2010.
55. Karuna Subramaniam, John Kounios, Todd B Parrish, and Mark Jung-Beeman. A brain mechanism for facilitation of insight by positive affect. Journal of Cognitive Neuroscience, 21(3):415-432, 2009.
56. Dennis Q Truong, Greta Magerowski, George L Blackburn, Marom Bikson, and Miguel Alonso-Alonso. Computational modeling of transcranial direct current stimulation (tdcs) in obesity: impact of head fat and dose guidelines. NeuroImage: Clinical, 2013.
57. Mauricio F Villamar, Pakorn Wivatvongvana, Jayanton Patumanond, Marom Bikson, Dennis Q Truong, Abhishek Datta, and Felipe Fregni. Focal modulation of the primary motor cortex in fibromyalgia using 4×1-ring high-definition transcranial direct current stimulation (HD-tDCS): immediate and delayed analgesic effects of cathodal and anodal stimulation. The Journal of Pain, 2013.
58. Dieter Wallach and Christian Lebiere. Conscious and unconscious knowledge: Mapping to the symbolic and subsymbolic levels of a hybrid architecture. In L. Jimenez, editor, Attention and Implicit Learning. John Benjamins, Amsterdam, Netherlands, 2003.
59. Javadi, A. H., & Walsh, V. (2012). Transcranial direct current stimulation (tDCS) of the left dorsolateral prefrontal cortex modulates declarative memory. Brain Stimulation, 5(3), 231-241.
60. Patterson, Freda, Christopher Jepson, Andrew A. Strasser, James Loughead, Kenneth A. Perkins, Ruben C. Gur, Joseph M. Frey, Steven Siegel, and Caryn Lerman. "Varenicline improves mood and cognition during smoking abstinence." Biological Psychiatry 65, no. 2 (2009): 144-149.
61. Ahmed, Amir I A, Abdullah N A Ali, Cees Kramers, Linda V D Hirmark, David M. Burger, and Willem M A Verhoeven. "Neuropsychiatric adverse events of varenicline: a systematic review of published reports." Journal of Clinical Psychopharmacology 33, no. 1 (2013): 55-62.
62. A. Datta, M. Elwassif, F. Battaglia, and M. Bikson, "Transcranial current stimulation focality using disc and ring electrode configurations: Fem analysis," J Neural Eng, vol. 5, pp. 163-74, 2008.
63. Khedr, et al., "Effect of Anodal Versus Cathodal Transcranial Direct Current Stimulation on Stroke Rehabilitation: A Pilot Randomized Controlled Trial", Neurorehabil Neural Repair, 27: 592-601, 2013.
64. Zwissler, B., et al., "Shaping memory accuracy by left prefrontal transcranial direct current stimulation," The Journal of Neuroscience, 34(11), 4022-4026, 2014.

(2) PRINCIPAL ASPECTS

The present invention has three "principal" aspects. The first is a system for system for mapping user behavior to brain regions of interest. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein. The one or more processors may have an associated memory with executable instructions encoded thereon such that when executed, the one or more processors perform multiple operations. The associated memory is, for example, a non-transitory computer readable medium.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, or a field programmable gate array.

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface I 10, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may includes one or more of an input device 112 coupled with the address/data bus 102, wherein the input device 112 is configured to communicate information and command selections to the processor 100. In accordance with one aspect, the input device 112 includes an alphanumeric input device, such as a keyboard, that may include alphanumeric and/or function keys. Alternatively or in addition, the input device 112 may include an input device other than an alphanumeric input device. For example, the input device 112 may include one or more sensors, such as a camera for video or still images, a microphone, or a neural sensor. Other example input devices 112 may include an accelerometer, a GPS sensor, or a gyroscope.

In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
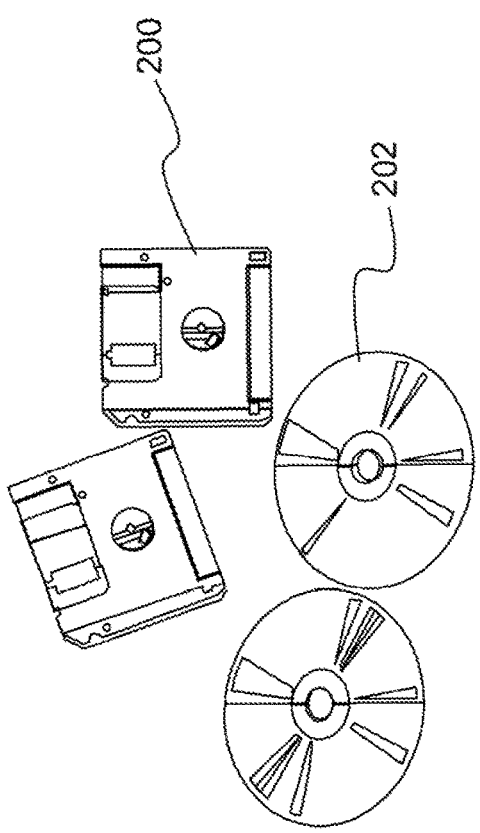
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) INTRODUCTION

Neurostimulation is an activation of part of the nervous system using electrodes (or microelectrodes). Non-limiting examples of neurostimulation include trans-cranial direct-current stimulation (tDCS), high definition (HD) tDCS, HD transcranial stimulation (HD-tCS), and transcranial magnetic stimulation. There is growing evidence that trans-cranial neurostimulation interventions can enhance key cognitive faculties associated with adaptive reasoning and problem solving including creativity (see Literature Reference No. 44), visual perception (see Literature Reference No. 6), visuospatial attention (see Literature Reference No. 51), and working memory functions (see Literature Reference No. 24). Trans-cranial direct-current stimulation (tDCS) is believed to either enhance or suppress the activation of neurons depending on the polarity of the electric field within the neural tissue (see Literature Reference No. 18). When this change in neural excitability is combined with endogenous neural activation during a person's task-generated activities, neural firing patterns are altered leading to both short-term and long-term changes in synaptic strengths.

Conventional two-electrode neurostimulations are impossible to focus on a targeted brain region, thus the resulting current flow through approximately half of the brain is not efficacious, especially when considering extended sessions (see Literature Reference No. 16). Soterix Medical developed the first technology capable of non-invasive, low-intensity, targeted electrotherapy, called high-definition trans-cranial direct-current stimulation (HD-tDCS) (see Literature Reference No. 62 for a description of HD-tDCS). This technology can increase, suppress, or drive functional, localized activity in target brain areas with a degree of precision and multi-regional parallelization never attainable using the standard two electrode tDCS.

Unlike deep brain stimulation and transcranial magnetic stimulation (TMS), HD-tDCS is designed to be portable and can be used at a clinic or at home with no pain, significant side effects, or risk of injury. Currents can be guided through the brain in an application- and subject-specific manner (see Literature Reference Nos. 10, 17, and 57). In comparison to conventional tDCS, HD-tDCS produces larger and longer-lasting effects in brain neuroplasticity (see Literature Reference Nos. 35 and 49). Despite the benefits, this technology has never been integrated with real-time, closed-loop, multi-modal sensing for directing neurostimulation, nor has HD-tDCS been directed through personalized and adaptive models.

In the system according to some embodiments of the present disclosure, a combination of cognitive-behavioral and functional-anatomical modeling are employed to provide comprehensive mapping from user behavior to brain regions of interest for neurostimulation patterns as described in further detail below.

Non-model-driven neurostimulation methods have been shown to enhance cognitive faculties such as inhibitory control (anodal PFC (prefrontal cortex) stimulation increasing activity (see Literature Reference No. 101)), working memory-anodal left-dlPFC (dorsolateral PFC (see Literature Reference No. 9), planning ability-(cathodal/anodal dlPFC (see Literature Reference No. 21)), task shifting (anodal dlPFC & M1) (see Literature Reference No. 39), feature categorization and cognitive control (cathodal left (see Literature Reference No. 41)), insight (anterior temporal lobe) (see Literature Reference No. 13), and diminished cognitive control (Left-PFC) (see Literature Reference No. 14). Although providing groundwork for functional assignments, and showing promising results, these singular neurostimulation studies have not tested enhancement effects across multiple brain regions, networks, dynamic activities or measured enhancement generalization or duration.

Additionally, previous works have not personalized stimulation protocols through cognitive-behavioral and functional-anatomical models for peak performance and maximal benefit. Further, the overall effectiveness of treatment has been limited by a lack of personalization and real-time brain state-driven closed-loop feedback. Those efforts to personalize neurostimulation from computational models have been limited to purely anatomical models (see Literature Reference Nos. 2 and 3).

(4) SPECIFIC DETAILS OF THE INVENTION

The system according to some embodiments of the present disclosure combines revolutionary work in high-definition (HD)-neurostimulation with personalized model-driven behavioral training to induce peak performance and lasting changes to the underlying neural systems, causing increased abilities in a variety of possible areas, including, but not limited to adaptive reasoning, problem solving, memory enhancement, rehabilitation after traumatic brain injury, improved executive function and motor performance.

Figure 3:
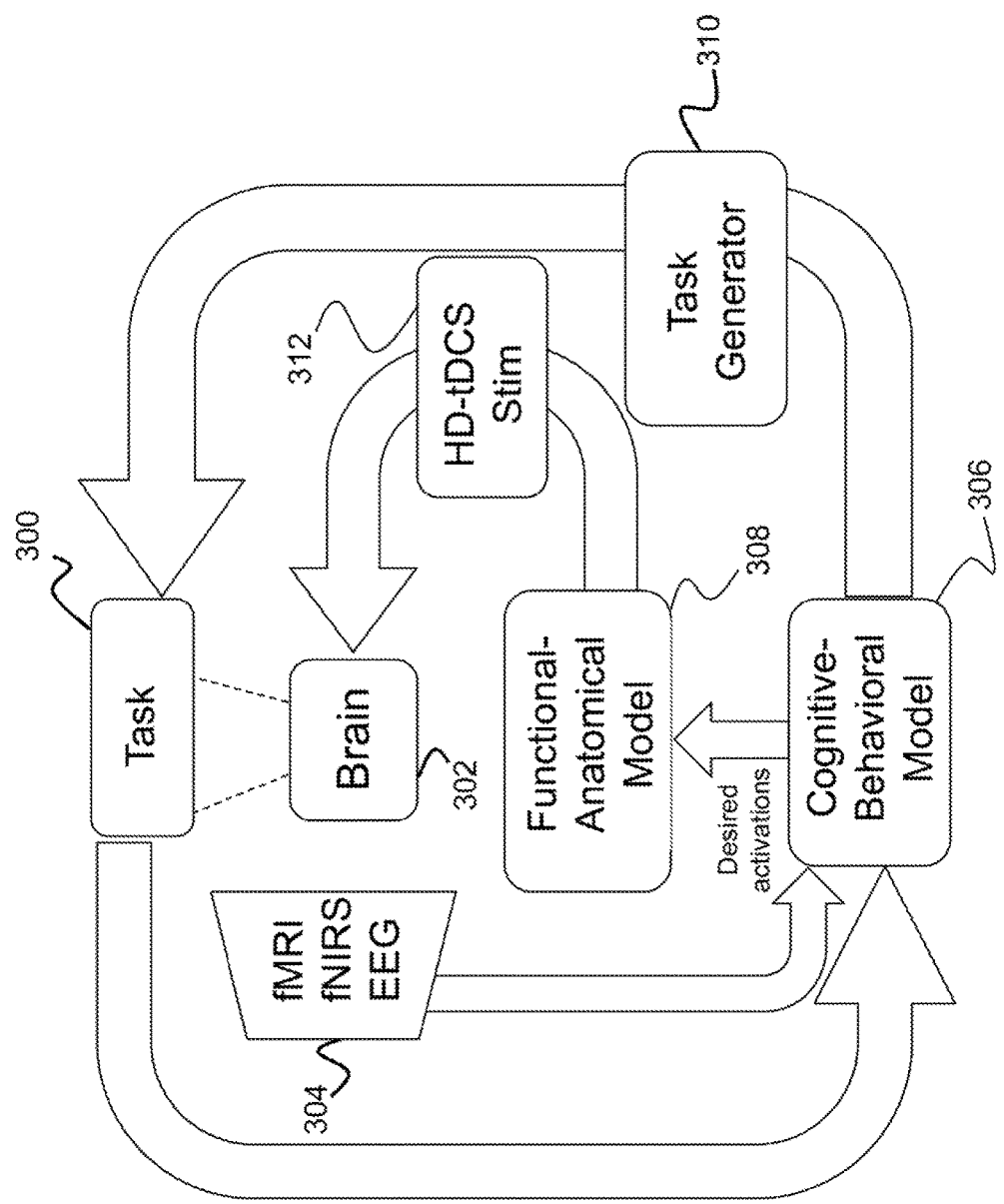
FIG. 3 is an illustration of the creation of personalized models based on sensed brain activity according to some embodiments of the present disclosure.

With current state-of-the-art trans-cranial direct-current stimulation (tDCS), enhancement effects show promise but vary drastically across subjects, some even declining in performance. The present invention solves this problem by using a personalized method that will improve the desired neural functions using multiple innovations as follows. As depicted in FIG. 3, users will perform behavioral tasks 300 while brain 302 activity is sensed by neuroimaging, non-limiting examples of which include fNIRS (functional near-infrared spectroscopy), EEG (electroencephalogram), and/or functional magnetic resonance imaging 304. Coupled cognitive-behavioral models 306 and functional-anatomical models 308 prescribe behavioral tasks and patterns of neurostimulation (via a task generator 310) to modify brain 302 region activity to improve performance in the desired region, and HD-neurostimulation (i.e., HD-tDCS stimulation 312) precisely targets those regions. Transcranial direct current stimulation (tDCS) functions by sending constant, low direct current through electrodes attached with the head of a human subject. When these electrodes are placed in the region of interest, the current induces intracerebral current flow. This current flow then either increases or decreases the neuronal excitability in the specific area being stimulated based on which type of stimulation is being used.

During training, EEG and fNIRS 304 provide feedback on a user's response to stimulation (i.e., HD-tDCS stimulation 312), while the coupled models (the cognitive-behavioral 306 and functional-anatomical 308 models) adapt to reflect individual differences, performance gains, and personalize training for peak performance for each individual. These causal models connect performance with explanatory and predictive mechanisms. Users will continue to use the system until the individual peak performance is obtained.

(4.1) Concept of Operation

Figure 4:
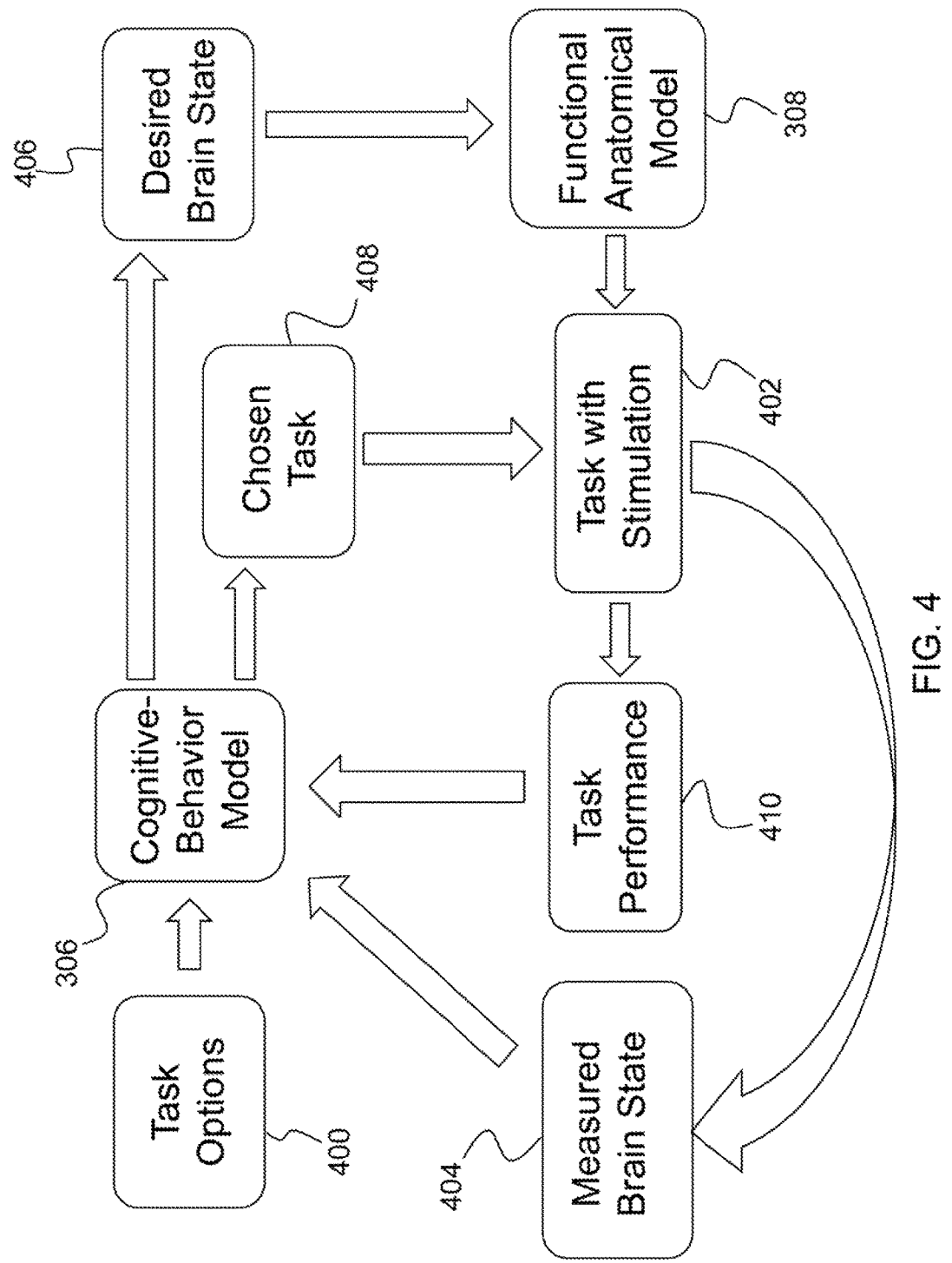
FIG. 4 is an illustration of functions of cognitive-behavioral and functional-anatomical models according to some embodiments of the present disclosure.

The basic concept of operation, shown in FIG. 4, is a multi-step process of choosing the correct behavioral task from a set of task options 400, stimulating the correct brain areas (i.e., task with stimulation 402), measuring the changing brain states 404, and modifying the personalized model (cognitive-behavior model 306 and functional-anatomical model 308). The correct brain areas are selected using the cognitive-behavioral model 306.

Users first must determine the type of cognitive improvement they desire (i.e., desired brain state 406). Non-limiting examples of cognitive improvement include increased working memory capacity, increased motor reaction times, and increased decision making performance. Once this has been chosen the cognitive-behavioral model 306 will determine what task (i.e., chosen task 408) would be best suited for such improvement. A non-limiting example of a chosen task 408 is aircraft control learning (i.e., learning to fly a plane). The functional-anatomical model 308 then determines what stimulation protocol to use for the given task (i.e., task with stimulation 402). For example, for working memory improvement, anodal stimulation of the right dlPFC can be used, as described in Literature Reference No. 64. The first time stimulation occurs the stimulation will be a general task specific stimulation and the models will adapt to the personal behavioral responses to the task. As a non-limiting example of a general task specific stimulation, working memory (a general cognitive faculty) can be trained with an N-back task and dlPFC stimulation. As the user performs tasks (i.e., task with stimulation 402) the brain state is measured (i.e., measured brain state 404) by multiple neural imaging modalities (fNIRS, EEG and/or fMRI (functional magnetic resonance imaging)). The cognitive-behavior model 306 will look for changes in brain states (i.e., measured brain state 404) as the behavioral tasks (i.e., task with stimulation 402) are performed by the user, suggesting new tasks as well as identifying regions of interest to be stimulated in task with stimulation 402 that are personalized for the current user based on their previous brain states (i.e., measured brain state 404).

The process according to some embodiments of the present disclosure comprises task selection (i.e., chosen task 408), brain area identification using the cognitive-behavioral model 306, a stimulation protocol (i.e., task with stimulation 402), analysis of task performance 410 (e.g., percentage of correct responses), and brain state measurement and analysis (i.e., measured brain state 404). The process repeats as the user improves in their desired area of cognitive enhancement.

(4.2) Multi-Modal Sensor Integration

The adaptive stimulation approach according to some embodiments of the present disclosure incorporates two modes of brain monitoring to facilitate feedback as the intervention takes place. The first is to use EEG to monitor dynamic brainwave power in the alpha and gamma frequency bands over the anterior cingulate region. This should indicate whether a subject is already predominately in an analytic or insight mode, as described in Literature Reference No. 32. The second is to use fNIRS to monitor activity in the prefrontal network. fNIRS monitoring of the prefrontal cortex has been shown to provide a good indication of cognitive workload (see Literature Reference No. 8).

Figure 8:
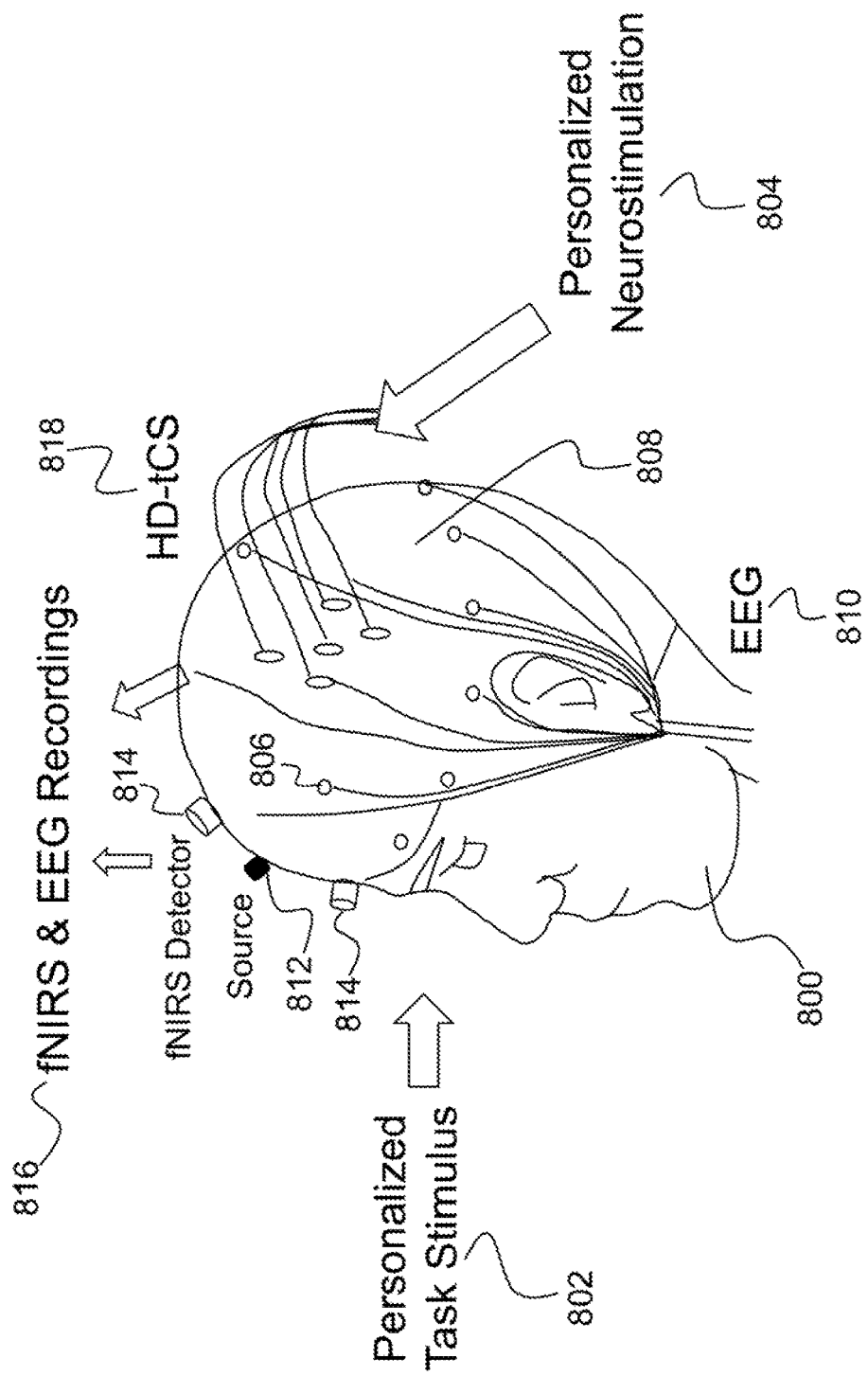
FIG. 8 is an illustration of the targeted change of brain states according to some embodiments of the present disclosure.

Unique advances have been developed to allow both EEG and fNIRS data to be collected during the stimulation intervention. For example, HD-tCS (high definition transcranial stimulation) electrodes are the same form factor as EEG electrodes and can be placed on the same head cap (or headband), as shown in FIG. 8. Interference between electrical stimulation currents and EEG is avoided by alternating the timing of the stimulation and EEG data capture switching up to 250 Hertz (Hz). This ensures sufficient EEG data can be collected below the Nyquist limit of 125 Hz while alternating current (AC) stimulation is provided. In this way, one can collect snippets of EEG data throughout the stimulation period without interference. Although any current stimulation produces increased blood flow on the scalp that can interfere with the fNIRS infrared signal, there are ways to process the fNIRS data to minimize sources of noise so that it can be used in conjunction with tCS (see Literature Reference Nos. 1, 26, 27, and 31 for descriptions of processing fNIRS data).

Figure 5:
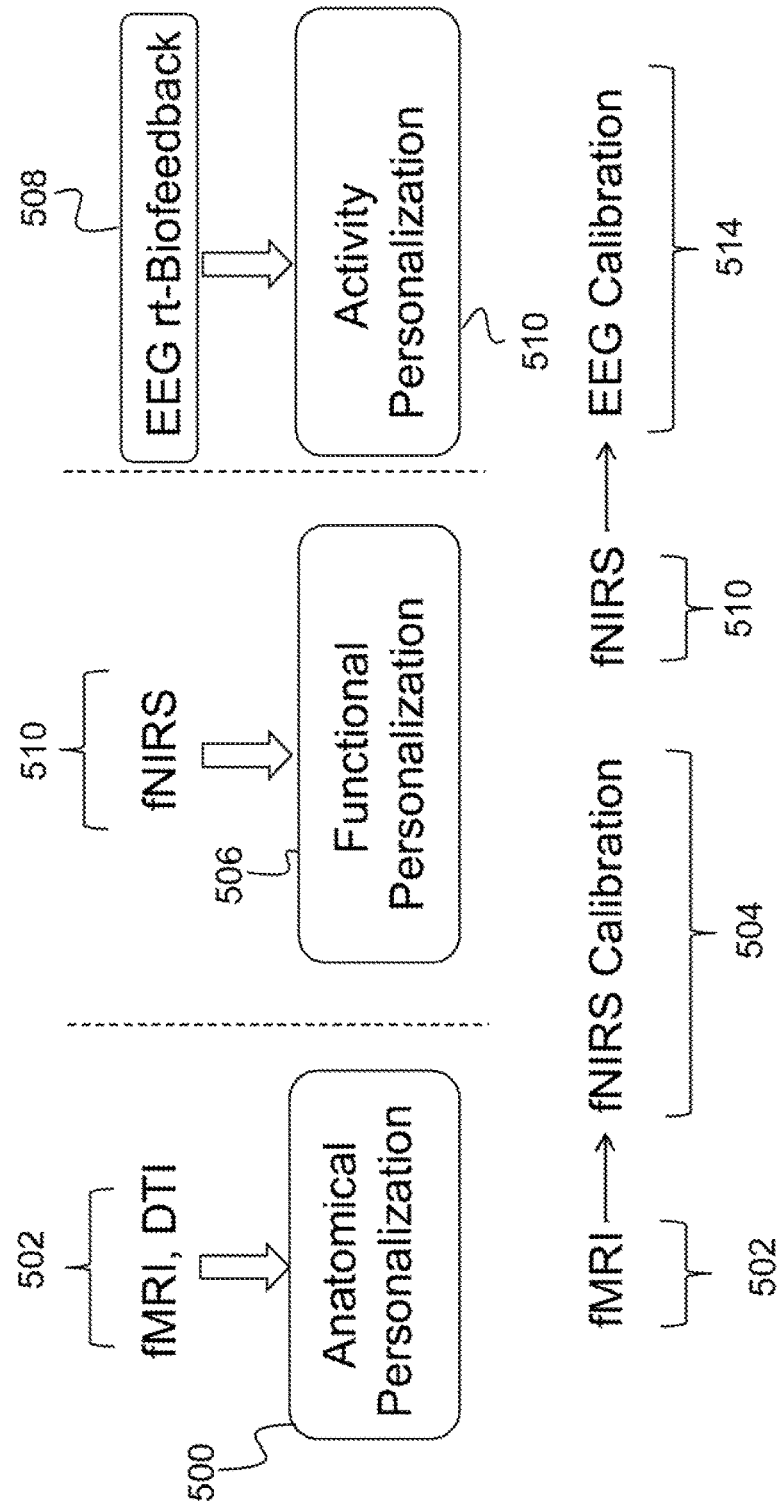
FIG. 5 is an illustration of multi-modal brain-state detection according to some embodiments of the present disclosure.

FIG. 5 depicts multi-modal brain-state detection. Targeted change of brain states is achieved by simultaneous excitation from task-generated activity while providing stimulation current. Anatomical personalization 500 occurs via functional magnetic resonance imaging (fMRI) and diffusion tensor imaging (DTI) mapping of individual's brains (fMRI: DTI 502). The three-dimensional (3D) volumes of the individual's brain structure and connectivity are used to calibrate the fNIRS sensing locations (i.e., fNIRS calibration 504) for real-time functional personalization 506. The EEG and real-time biofeedback system (EEG rt-Biofeedback 508 can be used in tandem to personalize stimulations (i.e., activity personalization 510) for detected functional frequencies in the ROIs derived from the fMRI/DTI 502. Additionally, fNIRS techniques 512 can be used for EEG calibration 514.

(4.3) Neurostimulation Parameter Space

Described herein is the use of HD-tDCS to drive individualized spatiotemporal stimulation pattern "montages" of regional activities (direct current (DC) stimulation) and complex region dynamics (alternating current (AC) stimulation) to activate or suppress specific target brain regions, networks, and dynamic states to optimize behavioral performance. By personalizing these stimulations though a combination of individualized cognitive-behavioral 306 and functional anatomical models 308, one can reduce the high variability seen with standard tDCS and ensure that each user is trained to engage the most optimal brain states and behavioral strategies (see Literature Reference No. 56).

Recent work has shown the importance of interactions between brain regions. The prefrontal cortex, for example, can act as a top-down filter to reduce distractions from bottom-up sensory inputs (see Literature Reference No. 46). At certain times, suppression of this filtering action may be beneficial to creative problem solving (e.g., by allowing competing hypotheses to be entertained). Modulating interactions between multiple brain regions requires the ability to simultaneously target numerous modal regions across the brain using region-specific stimulation protocols, which the system according to some embodiments of the present disclosure provides. This ability, combined with the model-driven stimulus generation according to some embodiments of the present disclosure, provides the needed flexibility to enhance the diverse set of cognitive faculties involved in solving problems in information-rich environments in high performing adults.

The HD-tCS system according to some embodiments of the present disclosure will support 9 DC/AC stimulation channels and 32 EEG channels for concurrent data collection (interleaved up to 250 Hz). The stimulation channels will support any combination of three different types of HD-tCS. Direct Current Stimulation (HD-tDCS) is used to inhibit or excite targeted functional brain regions. Alternating Current Stimulation (HD-tACS) induces oscillatory patterns of neural activity with target amplitudes, frequencies, and phases. Random Noise Stimulation (HD-tRNS) will promote neural plasticity (see Literature Reference Nos. 19, 42, 48, and 49).

(4.4) Model-Driven Stimulus Generation

Reasoning strategies and brain states may vary from one person to the next during problem solving, and HD-tCS has the ability to precisely apply neurostimulation with high resolution to induce personalized brain states. A generic neurostimulation is inappropriate; therefore, the present invention is model-based, and the models adapt during training from subject-specific fMRI, fNIRS, and EEG data. The cognitive-behavioral model 306 and the functional anatomical model 308, account for individual differences from a cognitive and an anatomical perspective, respectively, and determine a combination of electrode currents to produce on a subject's scalp so as to modulate target brain regions.

Figure 6:
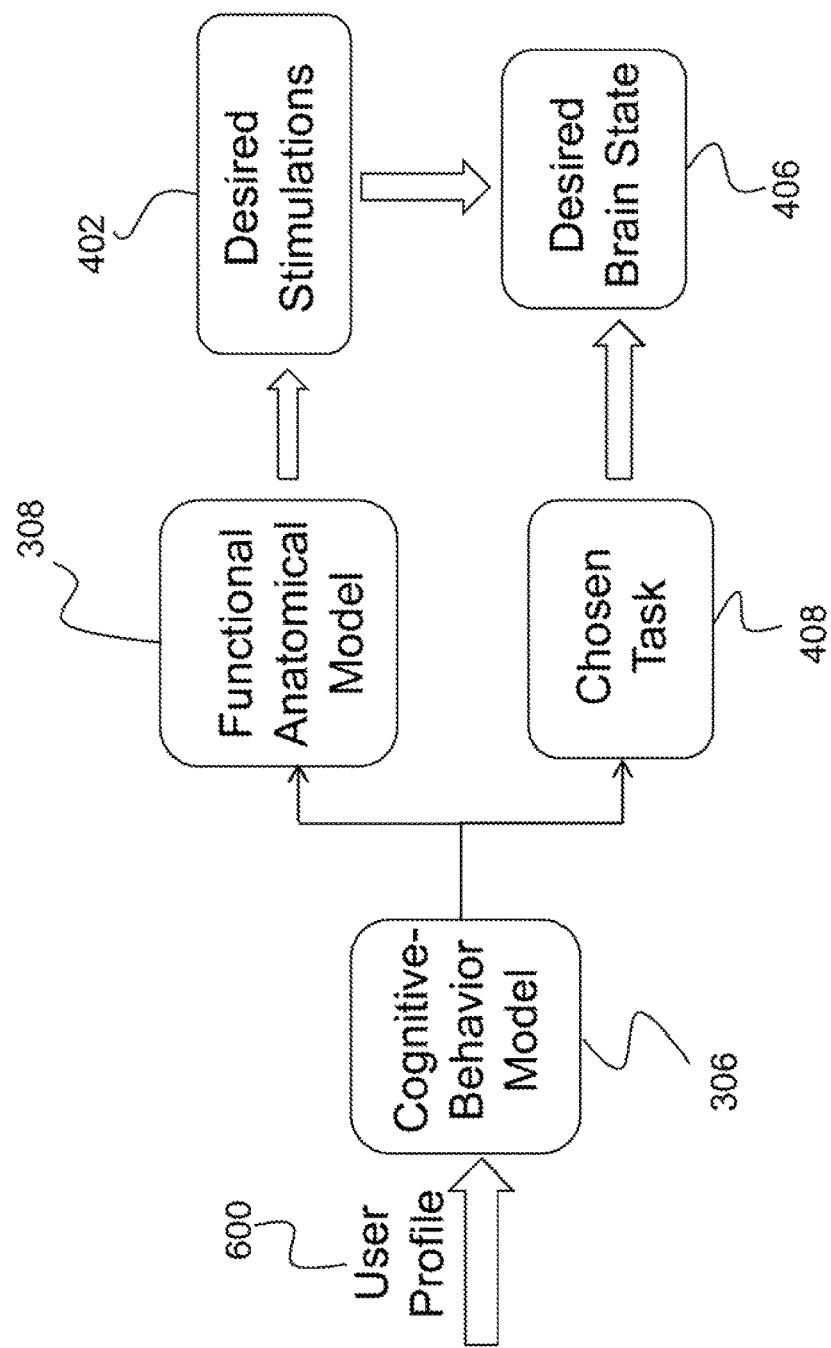
FIG. 6 is an illustration of targeted modulation of brain states via personalized cognitive and anatomical models according to some embodiments of the present disclosure.

FIG. 6 illustrates personalized cognitive and anatomical models direct the simultaneous production of HD-neurostimulations and behavioral training tasks to enable targeted modulation of specific brain regions, networks, and dynamic states. The first stage of modeling assesses behavioral performance deficiencies in healthy high-performing adults (having a user profile 600) and associates them with activation states in various brain regions. Non-limiting examples of behavioral performance deficiencies include lower working memory capacity, decreased set-shifting abilities, and cognitive biases that decrease the desired task performance (element 410). To initialize a phenotypic cognitive-behavioral model 306, the subject is engaged in a battery of cognitive tasks while being scanned with fMRI, and the performance is used to parameterize the cognitive-behavioral model 306. Literature Reference Nos. 12 and 24 describe non-model examples of behavioral tasks that could inform the cognitive-behavioral model of the present invention. This model will be implemented in a cognitive simulator (such as ACT-R described in Literature Reference No. 12). Once parameterized, the model predicts the subject's performance over the full spectrum of related tasks (see Literature Reference No. 11). Using identified weaknesses (e.g., limited working memory capacity, slow reaction times), the cognitive-behavioral model 306 will then be used to assemble a set of training tasks (task options 400 in FIG. 4), and for each task it will search for the desired "target" brain states (element 406), which is the state measured during peak behavioral performance during personalization that will yield the greatest estimated improvement in overall performance on the new task.

The second stage of modeling selects one of the training tasks at a time (element 408) to present to the subject, along with its associated target brain state (element 406). Three-dimensional (3D) functional-anatomical models 308, such as the Virtual Brain described in Literature Reference No. 40, capture both shape and conductance of tissues above and beneath the skull. Functional-anatomical models 308 associate functional brain regions for the target brain state (element 406) to specific physical locations within the skull and provide a means to determine the HD-tCS electrode currents needed to reach these regions effectively. This functional-anatomical model 308 must be initialized from a user's fMRI scan, but during the training regimen it is adapted based on fNIRS sensing, which provides a lower-cost rough approximation to fMRI data.

Given a set of brain regions designated for intervention and the desired activations of these regions, the functional-anatomical model 308 can derive the needed electrode currents and polarities to induce the target brain state (element 406). The stimulation is applied while the subject is engaged in the selected task (element 408). The method according to some embodiments of the present disclosure utilizes three primary categories of behavioral training and assessment tasks. The first category is a task from primary reasoning and problem solving, such as described in Literature Reference No. 24. The second category consists of tasks involving executive functions and the efficiency of switching between insight and analytical problem-solving strategies, such as described in Literature Reference Nos. 13 and 32. The third category involves reasoning about information rich environments presented in narratives about a complex topic, such as social norms of different cultures. However, the method according to some embodiments of the present disclosure does not depend on these specific tasks and is general to any form of cognitive or behavioral faculties.

Finally, the HD-tCS currents guide the subjects' neural activity during the tasks into states that assist subjects in realizing peak behavioral performance. Peak behavioral performance is assessed relative to experts in the field (e.g., pilots), and novice to expert transitions (e.g., learning to fly an airplane) are measured. Furthermore, these target brain states promote neural plasticity essential for improvement and persistence, while also enhancing the generalizability and retention of the cognitive skills developed during the training. Literature Reference Nos. 23, 25, and 37 postulate neural plasticity as the mechanism of action and demonstrate behavioral enhancement effects.

(4.5) Stimulus Adaptation and Neurofeedback

The third element of the method according to some embodiments of the present disclosure is to dynamically alter the stimulus currents based on sensor feedback of a subject's brain states both before and during engagement in behavioral tasks. The system described herein manipulates the oscillatory dynamics present in neural activity of specific brain regions in order to train and assist users in flexibly switching between modes of problem solving. The present invention functions by incorporating Alternating Current stimulation (HD-tACS), at gamma-band frequencies (~40 Hz) for activation and alpha-band frequencies (~10 Hz) for suppression, into a feedback loop that involves real-time sensing from both EEG and fNIRS. For the first time, data from both modalities is used during the course of transcranial stimulation.

Figure 7:
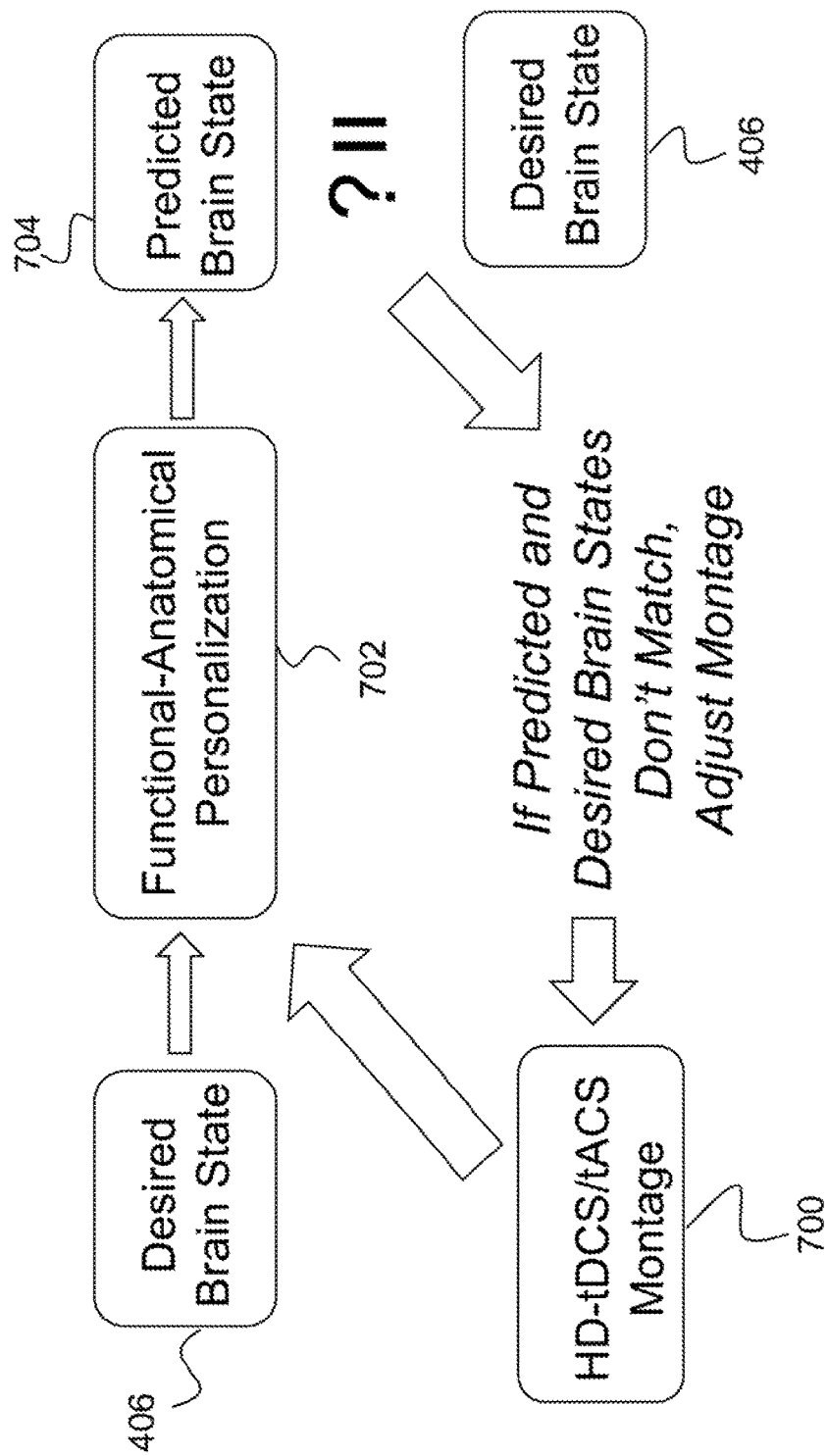
FIG. 7 is an illustration of personalized functional-anatomical models targeting neurostimulations for optimal brain state induction according to some embodiments of the present disclosure.

FIG. 7 depicts personalized functional-anatomical models targeting HD-neurostimulations for optimal brain state induction. As described above, HD-tDCS is used to drive individualized spatiotemporal stimulation pattern "montages" (i.e., HD-tDCS/tACS montage 700) of regional activities (DC stimulation) and complex region dynamics (AC stimulation) to activate or suppress specific target brain regions, networks, and dynamic states to optimize behavioral performance. Functional-anatomical personalization 702 (using the functional-anatomical models 308) attempts to have a predicted brain state 704 match the desired brain state 406 by determining the HD-tCS electrode currents (or HD-tDCS/tACS montage 700) needed to reach the desired brain regions effectively. If the predicted brain state 704 does not match the desired brain state 406, then the HD-tDCS/tACS montage 700 is adjusted by the functional-anatomical models 308 until a match is realized.

In order to solve complex real-world problems, individuals need to be adaptive and use a combination of problem-solving strategies (see Literature Reference Nos. 32 and 52). However, most people tend to have a natural predilection toward using one strategy or the other (see Literature Reference No. 33), and they have difficulty switching between them. Recent neuroimaging research has identified differences in brain states associated with analysis and insight (see Literature Reference No. 32). For example, insight solving involves a burst of activity in the right temporal lobe (see Literature Reference No. 29). Immediately prior to the presentation of an expected problem, subsequent insight solving is associated with elevated activity in the anterior cingulate and bilateral temporal lobes (see Literature Reference No. 34).

The real-time, closed-loop, multi-modal sensing of the system according to some embodiments of the present disclosure informs the cognitive-behavioral 306 and functional-anatomical 308 models for guided, adaptive and personalized neurostimulation to steer users toward these desired brain states 406. There are two key benefits of this capability. First, it increases the efficiency and efficacy of traditional neurostimulation and neurofeedback training, in which a subject will learn to "mentally steer" his or her brain state towards one of two target states. Second, it allows the induction of the desired target brain states 406 while a user is actively engaged in behavior, a capability that is infeasible during traditional neurofeedback training.

The method of adaptive stimulation according to some embodiments of the present disclosure facilitates a more flexible switching between modes of problem solving. For example, the method can induce the analytic brain state in subjects by stimulating their anterior cingulate region with alpha frequencies to decrease activity (see Literature Reference No. 50). This reduces the brain's monitoring of competing solution possibilities, resulting in a focused analytic strategy that follows the dominant, obvious path to solution (see Literature Reference Nos. 34 and 55). As cognitive workload increases, presumably because the subject is "stuck" (i.e., does not increase their skill level given additional training with respect to other subjects on this task) and can't make further progress, the system guides the user/subject to enter the insight brain state and then resume the task. This involves the cognitive-behavioral 306 and functional-anatomical 308 models stimulating the anterior cingulate region with gamma frequencies to increase activity. This will sensitize users to competing, nonobvious solution possibilities—"long shot" ideas. When the anterior cingulate detects weak, unconscious ideas, it can signal the dorsolateral PFC to switch to an idea (see Literature Reference No. 45) resulting in an insight (see Literature Reference No. 29).

(4.6) Model-Driven Neurostimulation Parameter Selection (4.6.1) Target and Predicted Brain States The cognitive-behavioral models 306 predict both level and flow of activation within and between regions of interest in the brain that are necessary to maximize learning and task performance. These regions and spread of activity will be personalized based on prior task performance along with previous model brain state predictions. The output will then inform the functional-anatomical model 308 to create patterns of HD-neurostimulation (element 402) appropriate to reach these brain regions at the target levels of activation.

The adaptivity of the model between training sessions is essential as the model must recognize performance that is not in line with its prediction (i.e., predicted state 704), determine the cause of the mismatch, and then adapt its training regimen to the new conditions. If a subject's performance worsens (as some do in non-personalized tDCS), the model adapts the task set given to the subjects or recommends new regional activation patterns until that individual improves. Juvina et al. used an ACT-R model to identify the benefit of early tDCS in a target search task, while also identifying the benefit of late tDCS in a change detection task (see Literature Reference No. 30). The model fit the differential influence and enhancement effect of both early and late tDCS and was compared to a control group which received no tDCS. This adaptation must also occur if the subject outperforms expectations, task performance increases faster than expected, and/or the task dependent brain activation patterns change.

(4.6.2) Model Personalization

As described above, personalization consists of two main approaches: setting architectural parameters (see Literature Reference No. 15 for a description of architectural parameters) and defining knowledge and skill structures (see Literature Reference No. 58 for a description of knowledge and skill structures). In the first approach, cognitive capacities are estimated from diagnostic tests and are then mapped onto architectural parameters. These parameters are then applied to the model to predict an individual's task performance and determine which tasks (and stimulations) will show the most generalized improvements. The latter approach to personalization will be to estimate the state of an individual's knowledge from the subject's performance (intelligent tutoring) and to determine which knowledge structures the participant has available and which new structures (e.g., skills) would maximize the participant's task performance.

FIG. 8 depicts achieving targeted change of brain states of a subject 800 by simultaneous excitation from task-generated activity (i.e., personalized task stimulus 802) while providing stimulation current (i.e., personalized neurostimulation 804) through electrodes 806 positioned in a cap 808 worn by the user 800. Electrical activity of the brain is recorded along the scalp of the user 800 via EEG 810. Additionally, the cap 808 includes an illumination source 812 and fNIRS detectors 814 (or detection sensors). fNIRS measures blood flow changes in the brain using near infrared light (emitted from the illumination source 812), which can pass into the brain to detect (with the fNIRS detectors 814) changes in blood oxygenation that can affect brain function and physiology. The set of fNIRS and EEG recordings 816 are then used to inform the functional-anatomical model 308 to create patterns of HD-tCS stimulation 818 in the user 800 via the cap 808 as part of the personalized neurostimulation 804. With HD-tCS, multiple smaller sized gel electrodes can be used to target specific cortical structures. While the description of a cap 808 is used as the means for providing stimulation and sensing electrical activity, any device that provides suitable contact with the scalp of the subject, such as a headband, may be utilized.

Figure 9A:
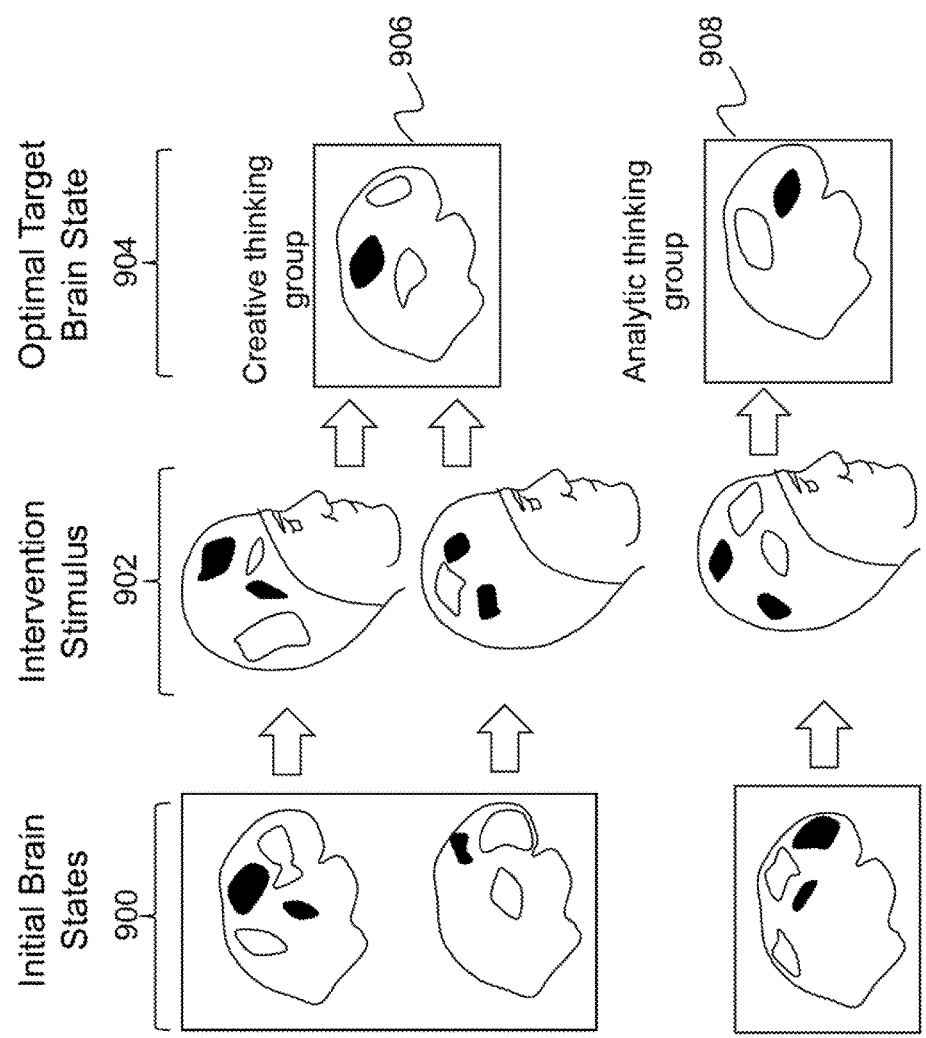
FIG. 9A is an illustration of optimal brain state induction according to some embodiments of the present disclosure.
Figure 9B:
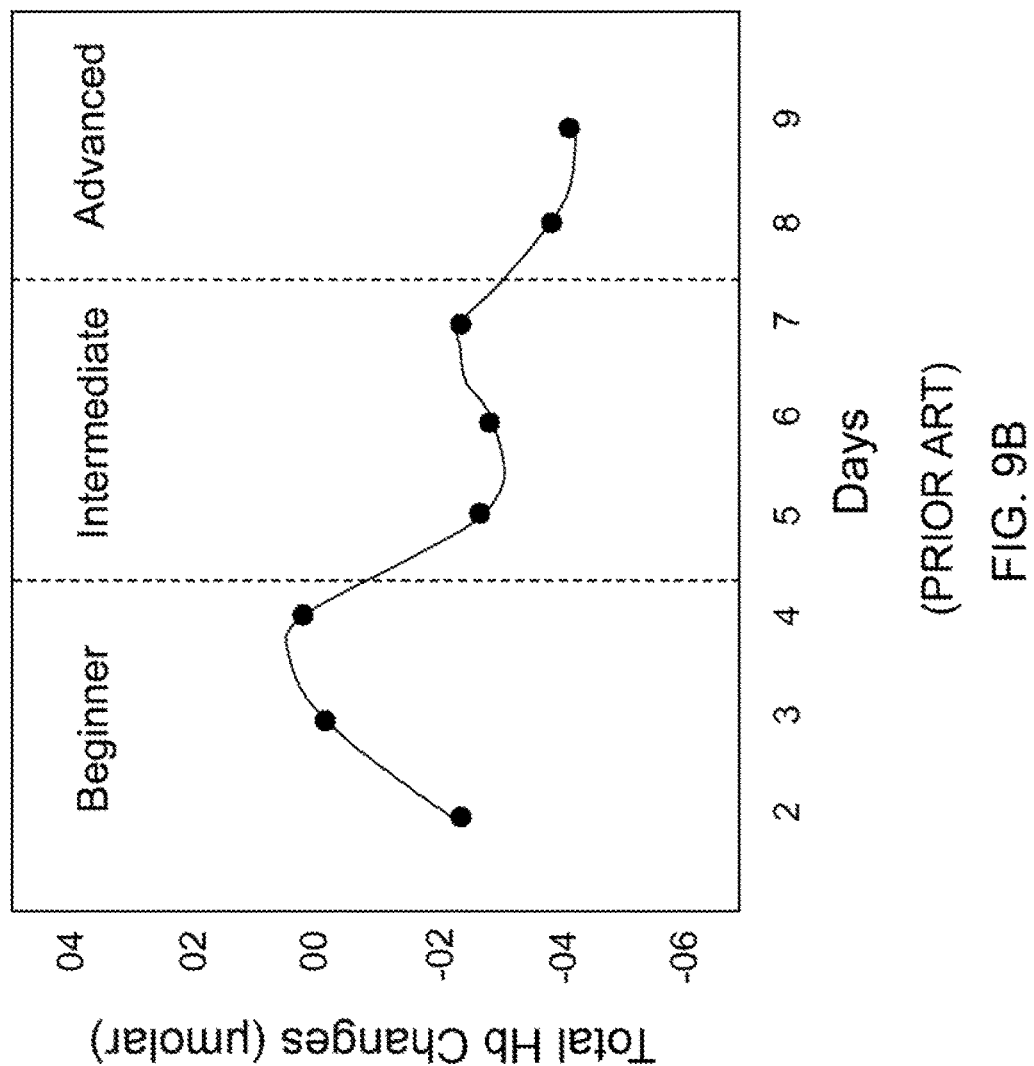
FIG. 9B is an illustration of prefrontal cortex activity during behavioral training according to prior art.

FIGS. 9A and 9B illustrate phenotypic personalization and expertise training according to some embodiments of the present disclosure. FIG. 9A depicts how the personalized adaptive method according to some embodiments of the present disclosure results in improved brain state induction for phenotypic subject categories. Initial brain states 900 undergo an intervention stimulus 902 to reach an optimal target brain state 904. As non-limiting examples, the phenotypic subject categories of an optimal target brain state 904 include a creative thinking group 906 and an analytic thinking group 908.

FIG. 9B illustrates fNIRS pilot data showing that prefrontal cortex activity (indicative of mental effort on task) generally reduces over the course of 9 days of behavioral training, after an initial increase. This is interpreted as increasing efficiency with expertise (see Literature Reference No. 8). Prefrontal cortex activity is measured in total hemoglobin (Hb) changes.

Figure 10:
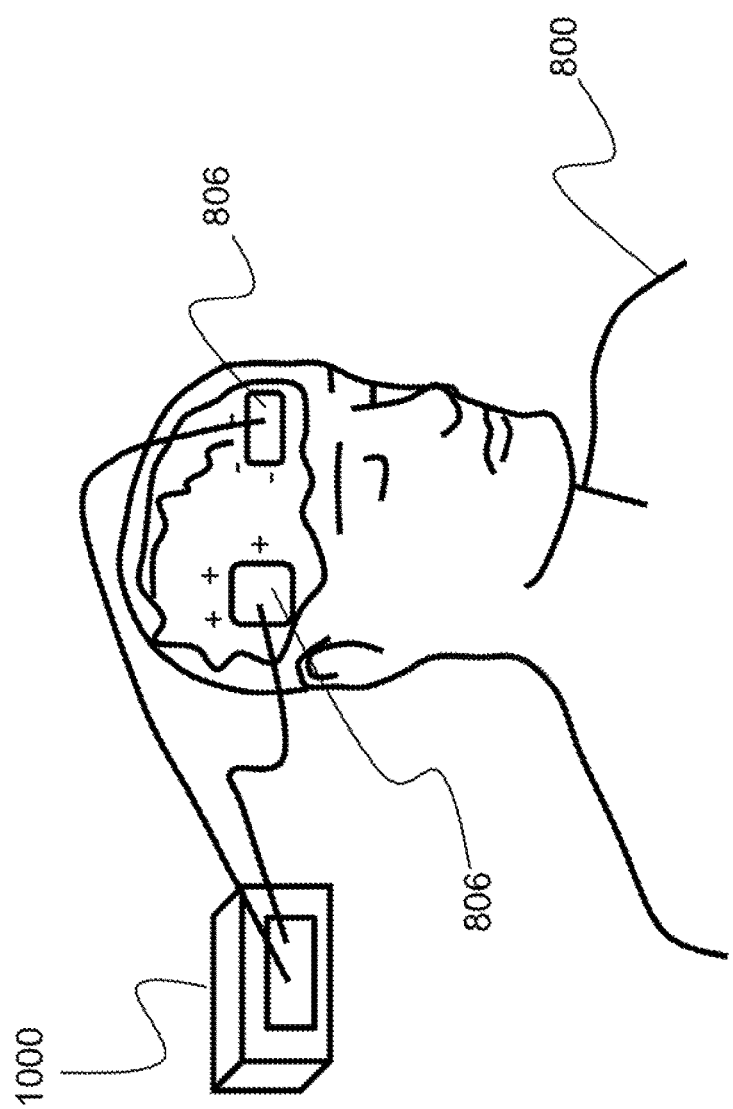
FIG. 10 is an illustration of a human subject receiving neurostimulation according to some embodiments of the present disclosure.

FIG. 10 illustrates a human subject 800 receiving neurostimulation according to some embodiments of the present disclosure. A device 1000 able to generate an electrical current delivers neurostimulation by applying a current through one electrode 806 (e.g., anode), and it flows through the brain to another electrode 806 (e.g., cathode).

What is claimed is:

1. A system for mapping behavior to brain regions of interest, the system comprising:
   one or more processors having associated memory with executable instructions encoded thereon such that when executed, the one or more processors perform operations of:
      selecting, using a functional-anatomical model coupled to a cognitive-behavior model, a set of high-definition neurostimulations, wherein the selected set of high-definition neurostimulations targets specific regions of a brain;
      sensing brain state data during application of the set of high-definition neurostimulations and performance of a selected behavioral task using at least one brain monitoring technique;
      assessing a set of behavioral performance deficiencies;
      associating the set of behavioral performance deficiencies with brain states in various brain regions;
      analyzing brain activity with a neuroimaging device as a plurality of behavioral tasks are performed, wherein the performance is used to parameterize the cognitive-behavior model;
      adapting the coupled functional-anatomical and cognitive-behavior models until desired brain state data are reached; and
      causing a device to deliver neurostimulation by applying an electrical current to the brain to induce the desired brain state data.

2. The system as set forth in claim 1, wherein the one or more processors perform operations of:
   implementing the cognitive-behavior model in a cognitive simulator;
   using the cognitive-behavior model to predict performance for a plurality of related behavioral tasks;
   using the cognitive-behavior model to generate a set of behavioral tasks; and
   for each task in the set of behavioral tasks, searching for the desired brain state data.

3. The system as set forth in claim 1, wherein the one or more processors perform operations of:
   associating, using the functional-anatomical model, brain regions for the desired brain state to specific physical locations; and
   selecting, using the functional-anatomical model, the set of high-definition neurostimulations to be applied to reach the associated brain regions effectively to induce the desired brain state data.

4. The system as set forth in claim 1, wherein the one or more processors further perform operations of:
   assessing, using the cognitive-behavior model, changes in brain state as a selected behavioral task in the set of behavioral tasks is performed; and
   outputting a new behavioral task in the set of behavioral tasks to be performed.

5. The system as set forth in claim 4, wherein the one or more processors further perform an operation of identifying, using the cognitive-behavior model, specific regions of brain to be targeted with a selected set of high-definition neurostimulations during performance of the new behavioral task based on a previous brain state.

6. The system as set forth in claim 1, wherein two brain monitoring techniques are used to sense changes in brain state, wherein the first brain monitoring technique is electoencephalography (EEG) to monitor brain activity in an anterior cingulate region of the brain, and wherein the second brain monitoring technique is functional near-infrared spectroscopy (fNIRS) to monitor brain activity in a prefrontal cortex region.

7. The system as set forth in claim 1, wherein the one or more processors further perform an operation of selecting, using a cognitive-behavior model, a behavioral task from a set of behavioral tasks that is suited for a desired brain state.

8. The system as set forth in claim 1, wherein the one or more processors further perform an operation of applying a set of high-definition neurostimulations during performance of a selected behavioral task.

9. The system as set forth in claim 1, wherein the one or more processors further perform operations of:
   implementing the cognitive-behavior model in a cognitive simulator; and
   using the cognitive-behavior model to predict performance for a plurality of related behavioral tasks.

10. The system as set forth in claim 1, wherein the one or more processors further perform operations of:
    using the cognitive-behavior model to generate a set of behavioral tasks; and
    for each task in the set of behavioral tasks, searching for the desired brain state data.

11. A computer program product for mapping behavior to brain regions of interest, the computer program product comprising:
    computer-readable instructions stored on a non-transitory computer-readable medium that are executable by a computer having one or more processors for causing the one or more processors to perform operations of:
       selecting, using a functional-anatomical model coupled to a cognitive-behavior model, a set of high-definition neurostimulations, wherein the selected set of high-definition neurostimulations targets specific regions of a brain;
       sensing brain state data during application of the set of high-definition neurostimulations and performance of a selected behavioral task using at least one brain monitoring technique;
       assessing a set of behavioral performance deficiencies;
       associating the set of behavioral performance deficiencies with brain states in various brain regions;
       analyzing brain activity with a neuroimaging device as a plurality of behavioral tasks are performed, wherein the performance is used to parameterize the cognitive-behavior model;
       adapting the coupled functional-anatomical and cognitive-behavior models until desired brain state data are reached; and causing a device to deliver neurostimulation by applying an electrical current to the brain to induce the desired brain state data.

12. The computer program product as set forth in claim 11, further comprising instructions for causing the one or more processors to perform operations of:

implementing the cognitive-behavior model in a cognitive simulator;

using the cognitive-behavior model to predict performance for a plurality of related behavioral tasks;

using the cognitive-behavior model to generate a set of behavioral tasks; and for each task in the set of behavioral tasks, searching for the desired brain state data.

13. The computer program product as set forth in claim 12, further comprising instructions for causing the one or more processors to perform operations of:

associating, using the functional-anatomical model, brain regions for the desired brain state to specific physical locations; and selecting, using the functional-anatomical model, the set of high-definition neurostimulations to be applied to reach the associated brain regions effectively to induce the desired brain state data.

14. The computer program product as set forth in claim 13, further comprising instructions for causing the one or more processors to perform operations of:

assessing, using the cognitive-behavior model, changes in brain state as a selected behavioral task in the set of behavioral tasks is performed; and outputting a new behavioral task in the set of behavioral tasks to be performed.

15. The computer program product as set forth in claim 14, further comprising instructions for causing the one or more processors to perform an operation of identifying, using the cognitive-behavior model, specific regions of brain to be targeted with a selected set of high-definition neurostimulations during performance of the new behavioral task based on a previous brain state.

16. The computer program product as set forth in claim 15, wherein two brain monitoring techniques are used to sense changes in brain state, wherein the first brain monitoring technique is electoencephalography (EEG) to monitor brain activity in an anterior cingulate region of the brain, and wherein the second brain monitoring technique is functional near-infrared spectroscopy (fNIRS) to monitor brain activity in a prefrontal cortex region.

17. A system for mapping behavior to brain regions of interest, the system comprising:

one or more processors having associated memory with executable instructions encoded thereon such that when executed, the one or more processors perform operations of:

assessing a set of behavioral performance deficiencies;

associating the set of behavioral performance deficiencies with brain states in various regions of a brain;

selecting, using a functional-anatomical model coupled to a cognitive-behavior model, a set of high-definition neurostimulations, wherein the selected set of high-definition neurostimulations targets specific regions of the brain;

analyzing brain activity with a neuroimaging device as a plurality of behavioral tasks are performed, wherein the performance is used to parameterize the cognitive-behavior model;

implementing the cognitive-behavior model in a cognitive simulator;

sensing brain state data during application of the set of high-definition neurostimulations and performance of a selected behavioral task using at least one brain monitoring technique;

adapting the coupled functional-anatomical and cognitive-behavior models until desired brain state data are reached;

using the cognitive-behavior model to predict performance for a plurality of related behavioral tasks;

using the cognitive-behavior model to generate a set of behavioral tasks;

for each task in the set of behavioral tasks, searching for the desired brain state; and causing a device to deliver neurostimulation by applying an electrical current to the brain to induce the desired brain state data.

18. The system as set forth in claim 17, wherein the one or more processors further perform operations of:

associating, using the functional-anatomical model, brain regions for the desired brain state to specific physical locations; and selecting, using the functional-anatomical model, the set of high-definition neurostimulations to be applied to reach the associated brain regions effectively to induce the desired brain state data.

19. The system as set forth in claim 17, wherein the one or more processors further perform operations of:

assessing, using the cognitive-behavior model, changes in brain state as a selected behavioral task in the set of behavioral tasks is performed; and outputting a new behavioral task in the set of behavioral tasks to be performed.

* * * * *